United States Patent [19]

Denoya et al.

[11] Patent Number: 5,707,839
[45] Date of Patent: Jan. 13, 1998

[54] **GENES ENCODING BRANCHED-CHAIN ALPHA-KETOACID DEHYDROGENASE COMPLEX FROM *STREPTOMYCES AVERMITILIS***

[75] Inventors: Claudio D. Denoya, Groton; Kim J. Stutzman-Engwall, East Lyme, both of Conn.

[73] Assignee: Pfizer Inc., New York, N.Y.

[21] Appl. No.: 470,892

[22] Filed: Jun. 6, 1995

Related U.S. Application Data

[62] Division of Ser. No. 168,602, Dec. 16, 1993, abandoned.

[51] Int. Cl.$^6$ .............................. C12P 17/18; C07H 17/08
[52] U.S. Cl. .................... 435/119; 536/7.1; 435/253.5; 435/76; 514/30
[58] Field of Search ........................ 424/93.2, 93.43; 435/69.1, 119, 235.3, 172.1, 320.1; 514/30; 536/7.1, 23.1

[56] References Cited

U.S. PATENT DOCUMENTS 5,077,278 12/1991 Hafner et al. ......................... 514/30
5,252,474 10/1993 Gewain et al. ...................... 435/172.3

FOREIGN PATENT DOCUMENTS 8703907 7/1987 WIPO.

OTHER PUBLICATIONS

Sykes et al, "Molecular Cloning of Genes Encoding Branched-Chain Keto Acid Dehydrogenase of *Pseudomonas putida*", J. Bacteriol. (1987)169: 1619–1625.

*Primary Examiner*—Robert A. Wax
*Assistant Examiner*—Daniel S. Mytelka
*Attorney, Agent, or Firm*—Peter C. Richardson; Gregg C. Benson; Robert F. Sheyka

[57] ABSTRACT

The present invention relates to novel DNA sequences that encode for the branched-chain alpha-ketoacid dehydrogenase complex of an organism belonging to the genus Streptomyces and to novel polypeptides produced by the expression of such sequences. It also relates to novel methods of enhancing the production of natural avermectin, of producing a *Streptomyces avermitilis* bkd mutant and of producing novel avermectins through fermentation.

2 Claims, 9 Drawing Sheets

FIG. 1

RIGHTWARD PRIMER

5'-AAGAATTCGAGCTCGGGCGACGGCGCCACCTCCGAGGGCGAC-3'

EcoRI  SacI

LEFTWARD PRIMER

5'-AAGGATCCTCTAGAGGTSSWGTGGKGGCCCGATSCGGWA-3'

BamHI  XbaI

```
TAC GTC TTC CCG ACC TAC CGC GAG CAC GGC GTC GCC TGG TCC GGC GTC GAC         54
 Y   V   F   P   T   Y   R   E   H   G   V   A   W   S   G   V   D
                                    27
CCC ACC AAC CTG CTC GGC ATG TTC CGC GGC GTG AAC AAC GGC GGC TGG GAT CCC    108
 P   T   N   L   L   G   M   F   R   G   V   N   N   G   G   W   D   P
                                    81
AAC AGC AAC TTC CAC CTC TAC ACG ATC GTC ATC GGC TCG CAG ACG CTG CAC        162
 N   S   N   F   H   L   Y   T   I   V   I   G   S   Q   T   L   H
                                   135
GCC ACC GGC TAC GCC ATG GGT ATC AAG GAC GTG GCC GAC TCG GAC GCC ATC        216
 A   T   G   Y   A   M   G   I   K   D   V   A   D   S   D   A   I
                                   189
GCC TAC TTC GGT GAC GGC TAC AAC GCC CAG GGT ATC GCC GCC GAA TCG GCC        270
 A   Y   F   G   D   G   Y   N   A   Q   G   I   A   A   E   S   A
                                   243
TTC TCC GCG GTC TCG AGC CCC GTC ACC CAG GTC ACC CGC GAC GTC TGC CCG AAC    324
 F   S   A   V   S   S   P   V   T   Q   V   T   R   D   V   C   P   N
                                   297
GCG ATC TCG GCG TAC CCG GGC TTC CCG GGC TTC CCG GAG AAG CAG GTC ACC CGC GTC GAC GGC  378
 A   I   S   A   Y   P   G   F   P   G   F   P   E   K   Q   V   T   R   V   D   G
                                   351
CAG GGC TAC GTC AGC CCC GGC TTC CCG AAG TGC CTC GAG CAG CTC TAC GAC GTA CTG GCC TGC  432
 Q   G   Y   V   S   P   G   F   P   K   C   L   E   Q   L   Y   D   V   L   A   C
                                   405
CTC GCC GTC ACC AAG TGC CTC GAG CGC GCC CGG CGC GCC GGC GAG GGG CCC ACG TTG        486
 L   A   V   T   K   C   L   E   R   A   R   R   A   G   E   G   P   T   L
                                   459
GTC GAG GCG TTC ACG
 V   E   A   F   T
```

```
    CTC GCC GAG TCG GGC ATC GTC GGC ACG GCG ATC GGT CTC GCC CTG CGC GGC TAC
27
     L   A   E   S   G   I   V   G   T   A   I   G   L   A   L   R   G   Y

CGG CCG GTG GTG GAG ATC CAG TTC GAC GGC TTC GTC TTC CCG GCG TAC GAC CAG
81                                                                         108
     R   P   V   V   E   I   Q   F   D   G   F   V   F   P   A   Y   D   Q

ATC GTC ACG CAG CTC GCG AAG ATG CAC GCG CGG GCG TCG GGC AAG ATC AAG CTC
135                                                                        162
     I   V   T   Q   L   A   K   M   H   A   R   A   S   G   K   I   K   L

CCC GTT GTC GTC CGC ATC CCG TAC GGC GGC GGC ATC GGC
189
     P   V   V   V   R   I   P   Y   G   G   G   I   G
```

FIG. 5

CD785
Limits:   3   194

```
CCG GTG TTC CTG GGC GGG CCG GAG ATC GCC CGC ATC ACG GAG CGC
 P   V   F   L   G   G   P   E   I   A   R   I   T   E   R     56

29
TGC TTC TAC CAC CTG GAG GCA CCC GTG CTG AGG GTC GGC TAC CAC GCC CCG
 C   F   Y   H   L   E   A   P   V   L   R   V   G   Y   H   A   P    110

83
TAT CCG CCG GCG CGT CTG GAA GAG TAC CTT CCG GGC CTT GAC CGG GTG CTC
 Y   P   P   A   R   L   E   E   Y   L   P   G   L   D   R   V   L    164

137
GAT GCC GTC GAC CGC TCG CTG GCG TAC TGA
 D   A   V   D   R   S   L   A   Y   *

```
CD786
Limits:       3      455
                            29                                                          56
AAC CAG GAG ATC GTC CTC AAG CAC TAT GTG AAC CTG GGC ATC GCG GCC ACC
 N   Q   E   I   V   L   K   H   Y   V   N   L   G   I   A   A   T
                                       83                                              110
CCG CGC GGT CTG ATC GTC CCG AAC ATC AAG GAC GCC CAC GCC AAG ACC GTG CCG
 P   R   G   L   I   V   P   N   I   K   D   A   H   A   K   T   V   P
                                      137                                              164
CAA CTG GCC GAG TCA CTG GGT GAG TTG GTG TCG ACG GCC CGC GAG GGC AAG ACG
 Q   L   A   E   S   L   G   E   L   V   S   T   A   R   E   G   K   T
                                      191                                              218
TCC CCG ACG GCC ATG CAG GGC ACG GTC ACG ATC AAC CCC GGC GAG TCC GCG ATC
 S   P   T   A   M   Q   G   T   V   T   I   N   P   G   E   S   A   I
                                      245                                              272
CGG CGT CGA CAC GGG GCC GAT CCT ATC CTC AAC CCC TGG GTC CAC AAG GGC GTT CTT
 R   R   R   H   G   A   D   P   I   L   N   P   W   V   H   K   G   V   L
                                      299                                              326
CTC GGC TTC CAG CAG CTC AAG CTC AGC TTC GAC CAT CGC CTG GTC AAG GTC ATC
 L   G   F   Q   Q   L   K   L   S   F   D   H   R   L   V   K   V   I
                                      353                                              380
CCC CGA CAG GTC ACC ACG CTG GCG GCC GTG GCG ATC CTG GAG CAG CCG AAG
 P   R   Q   V   T   T   L   A   A   V   A   I   L   E   Q   P   K
                                      407                                              434
GAG CTG GGC TCC AAG GTG CTG GAC GTG GCC GCG ATC CTG GAG CAG CCG AAG GGC
 E   L   G   S   K   V   L   D   V   A   A   I   L   E   Q   P   K   G
CGG CTG ATC ACC TGG GCC TAG .
 R   L   I   T   W   A   *
```

GENES ENCODING BRANCHED-CHAIN ALPHA-KETOACID DEHYDROGENASE COMPLEX FROM *STREPTOMYCES AVERMITILIS*

This is a division of application Ser. No. 08/168,602, filed on Dec. 16, 1993, now abandoned.

BACKGROUND OF THE INVENTION

The present invention relates to novel DNA sequences that encode for a branched-chain alpha-ketoacid dehydrogenase (BCKDH) complex of an organism belong to the genus Streptomyces. It also relates to the production of a *Streptomyces avermitilis* branched-chain alpha-ketoacid dehydrogenase (bkd)-deficient mutant by genetic engineering technology. The bkd-deficient mutant lacks branched-chain alpha-ketoacid dehydrogenase activity, and is useful for the fermentative production of novel (non-natural) avermectins.

*S. avermitilis* naturally produces eight distinct but closely related antiparasitic polyketide compounds named avermectins. The avermectin complex produced by *S. avermitilis* has four major components, A1a, A2a, B1a, and B2a, and four minor components, A1b, A2b, B1b, and B2b. The structure of the various components are depicted below.

methylbutyric acid or isobutyric acid. The designations "A" and "B" refer to avermectins wherein the 5-substituent is methoxy or hydroxy, respectively. The numeral "1" refers to avermectins wherein a double bond is present at the 22–23 position, and numeral "2" to avermectins having a hydrogen at the 22-position and hydroxy at the 23-position. Lastly, the C-25 has two possible substituents: the sec-butyl substituent (derived from the incorporation of S(+)-2-methylbutyric acid) is present in the avermectin "a" series, and the isopropyl substituent (derived from the incorporation of isobutyric acid) is present in the avermectin "b" series (for a review see Fisher, M. H. and Mrozik, H., 1984, "Macrolide Antibiotics", Academic Press, chapter 14).

By "natural" avermectins is meant those avermectins produced by *S. avermitilis* wherein the 25-position substituent is, as mentioned above, either isopropyl or sec-butyl. Avermectins wherein the 25-position group is other than isopropyl or sec-butyl are referred to herein as novel or non-natural avermectins.

One metabolic route to the natural alpha-branched-chain fatty acids in their CoA form is from the alpha branched-chain amino acids isoleucine and valine through a branched-chain amino acid transaminase reaction followed by a branched-chain alpha-ketoacid dehydrogenase reaction. (Alternatively, branched-chain fatty acyl-CoA derivatives

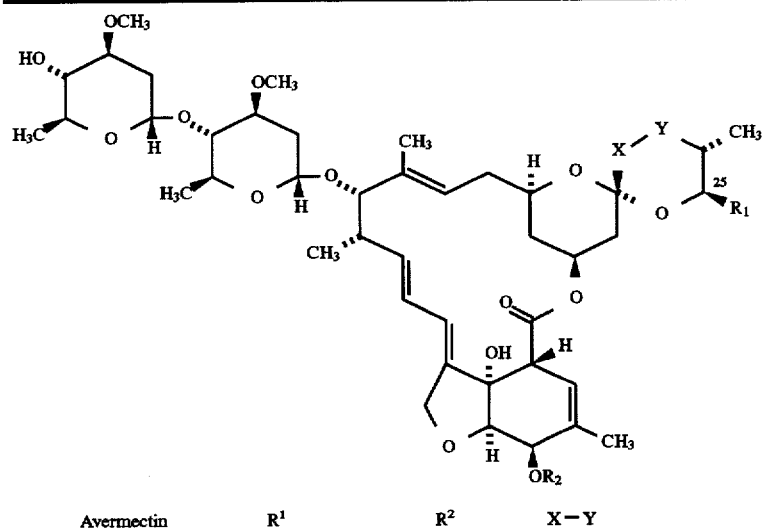

| Avermectin | R¹ | R² | X—Y |
|---|---|---|---|
| A1a | sec-butyl | Me | CH=CH |
| A1b | Isopropyl | Me | CH=CH |
| A2a | sec-butyl | Me | $CH_2-CH(OH)$ |
| A2b | Isopropyl | Me | $CH_2-CH(OH)$ |
| B1a | sec-butyl | H | CH=CH |
| B1b | Isopropyl | H | CH=CH |
| B2a | sec-butyl | H | $CH_2-CH(OH)$ |
| B2b | Isopropyl | H | $CH_2-CH(OH)$ |

The avermectin polyketide structure is derived from seven acetate, five propionate molecules, and one alpha-branched-chain fatty acid molecule, which is either S(+)-2- can arise from branched-chain alpha-ketoacids produced by de novo synthesis). These metabolic pathways are depicted below.

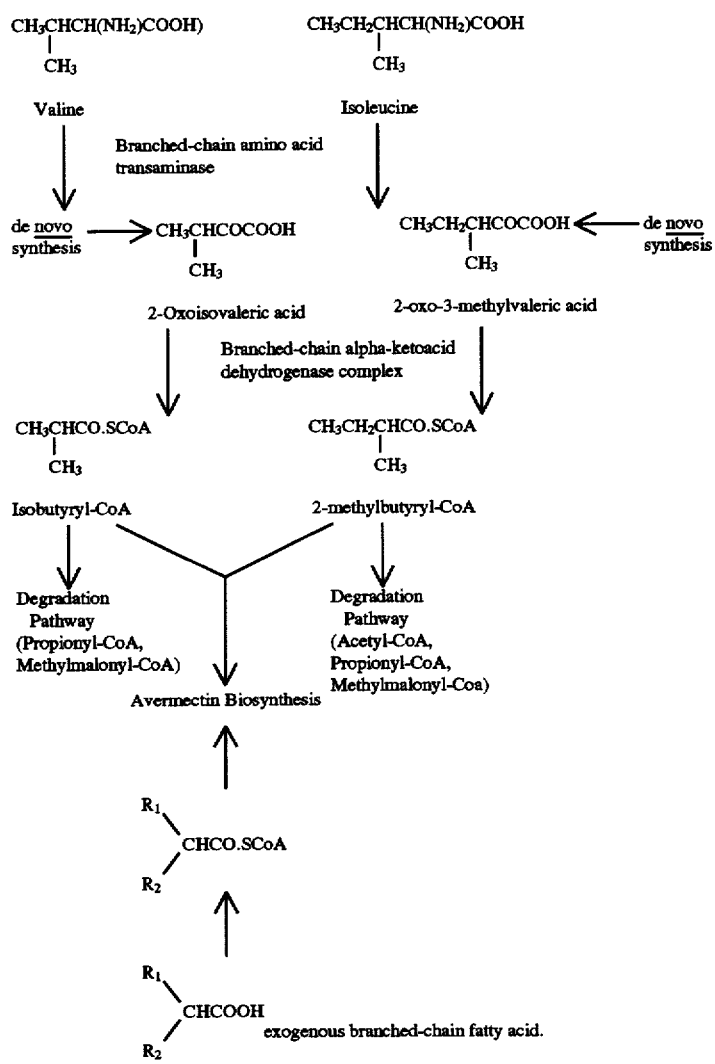

A mutant of *S. avermitilis* with no detectable branched-chain alpha-ketoacid dehydrogenase (BCKDH) activity in the last mentioned enzyme was previously isolated (Hafner et al., 1988, European Patent EP 284, 176, which issued on Oct. 20, 1993). The mutant was isolated following standard chemical mutagenesis of *S. avermitilis* strain ATCC 31272 in a screen searching for the absence of $^{14}CO_2$ production from $^{14}C$-1 labeled 2-oxoisocaproic acid substrate (leucine analog). The mutant is unable to synthesize natural avermectins except when the S(+)-2-methylbutyric acid or isobutyric acid or a precursor bearing the isopropyl or sec-butyl (S-form) group is added to the medium in which the mutants are fermented. The mutant is also capable of producing novel (non-natural) avermectins when fermented under aqueous aerobic conditions in a nutrient medium containing an exogenously added alternative carboxylic acid, such as cyclohexane carboxylic acid (CHC), or a precursor thereof, as indicated above.

To clone the genes that encode the branched-chain alpha-ketoacid dehydrogenase complex of *S. avermitilis* is highly desirable. Manipulation of these genes through recombinant DNA techniques should facilitate the production of natural and novel avermectins. For certain strains, increased titer of natural avermectins would be anticipated by increasing the copy number of the bkd genes. In addition, generation of an irreversibly blocked bkd strain, having BCKDH activity permanently deleted or modified by gene replacement, would be an improved alternative to the bkd mutant which was obtained, as mentioned before, by chemical mutagenesis.

The alpha-ketoacid dehydrogenase multienzyme complexes—the branched-chain alpha-ketoacid dehydrogenase (BCKDH) complex, the pyruvate dehydrogenase (PDH) complex, and the alpha-ketoglutarate dehydrogenase (KGDH) complex catalyze the oxidative decarboxylations of branched-chain alpha-ketoacids, pyruvate, and alpha-ketoglutarate, respectively, releasing CO2 and generating the corresponding Acyl-CoA and NADH (Perham, R. N., 1991, *Biochemistry*, 30: 8501–8512). Each complex consists of three different catalytic enzymes: decarboxylase (E1), dihydrolipoamide acyltransferase transacylase (E2), and dihydrolipoamide dehydrogenase (E3).

Branched-chain alpha-ketoacid dehydrogenase (BCKDH) is a multienzyme complex composed of three functional components, E1, the decarboxylase, E2, the transacylase, and E3, the lipoamide dehydrogenase. The purified complexes from *Pseudomonas putida*, *Pseudomonas aeruginosa*, and *Bacillus subtilis*, are composed of four polypeptides. The purified mammalian complexes also consist of four polypeptides, E1alpha, E1beta, E2, and E3. An alpha-ketoacid dehydrogenase complex has been isolated from *Bacillus subtilis* which has both pyruvate and branched-chain alpha-ketoacid dehydrogenase activities. This dual function complex oxidizes both pyruvate and branched-chain alpha-ketoacids for membrane phospholipids.

Cloning of prokaryotic branched-chain alpha-ketoacid dehydrogenase genes has been reported for Pseudomonas and Bacillus. In these systems it was found that the genes encoding the BCKDH were clustered in an operon. The genes of the BCKDH complex of *Pseudomonas putida* have been cloned and the nucleotide sequence of this region determined (Sykes et al., 1987, *J. Bacteriol.*, 169:1619–1625, and Burns et al., 1988, *Eur. J. Biochem*, 176:165–169, and 176:311–317). The molecular weight of E1alpha is 45289, of E1beta is 37138, of E2 is 45134, and of E3 is 48164. The four genes are clustered in the sequence: E1alpha, E1beta, E2, and E3. Northern blot analysis indicated that expression of these four genes occurs from a single mRNA and that these genes constitute an operon. There is a typical prokaryotic consensus promoter immediately preceding the start of the E1 alpha coding region that permits the constitutive expression of the Pseudomonas bkd genes. The initiator codon for the E1 beta coding region is located only 40 nucleotides downstream from the end of the E1 alpha open reading frame (ORF). In contrast, there is no intergenic space between the E1beta and E2 ORFs since the stop codon for the E1beta ORF is the triplet immediately preceding the initiator codon of the E2 ORF. The intergenic space between the E2 and the E3 ORFs is reduced to only 2 nucleotides. Therefore, the Pseudomonas bkd genes are tightly linked.

Similarly, the operon coding for the *Bacillus subtilis* BCKDH/PDH dual complex has been cloned (Hemila et al., 1990, *J. Bacteriol.*, 172:5052–5063). This operon contains four ORFs encoding four proteins of 42, 36, 48, and 50 kilodaltons (kDa) in size, shown to be highly homologous to the E1alpha, E1beta, E2, and E3 subunits of the Pseudomonas bkd cluster. The genes encoding the alpha and beta subunits of the E1 component of the dual BCKDH/PDH multienzyme complex from *Bacillus stearothermophilus* have also been cloned and sequenced (estimated molecular weights of the alpha and beta subunits are approximately 41,000 and 35,000, respectively) (Hawkins et al., 1990, *Eur. J. Biochem.*, 191:337–346).

Additionally, the sequences of a number of eukaryotic E1 alpha and beta BCKDH subunits (human, bovine, and rat) have been disclosed. Recently, an amino acid sequence comparison of all the published sequences known for both E1alpha and E1beta components of the PDH and the BCKDH complexes from multiple species was performed by computer analysis (Wexler et al., 1991, *FEBS Letters*, 282:209–213). Interestingly, several regions of the alpha and beta subunits were identified that are highly conserved not only in all PDHs so far described, but also in both prokaryotic and eukaryotic BCKDH complexes.

Also, recently, three genes encoding, respectively, the alpha (bkdA) and beta (bkdB) subunits of the E1 component, and the E2 (bkdC) component of a BCKDH complex from *Streptomyces avermitilis* were cloned, sequenced, and analyzed by using a heterologous gene expression system (Denoya, C. D., 1993, "Cloned genes encoding branched-chain alpha-ketoacid dehydrogenase complex from *Streptomyces avermitilis*", U.S. patent application Ser. No. 08/100, 518, filed Jul. 30, 1993). DNA sequence analysis showed the presence of putative transcriptional promoter sequences and bkd structural genes arranged as a cluster organized as follows: promoter sequence, E1-alpha (bkdA), E1-beta (bkdB), and E2 (bkdC) open reading frames. Additionally, the complete *S. avermitilis* bkdABC gene cluster was cloned downstream of the strong *Escherichia coli* T7 promoter for expression in an *E. coli* host. Similarly, the E1-alpha and E1-beta open reading frames (ORFs) were also cloned, either separately or together, downstream of the T7 promoter and each construction was tested for expression. These studies demonstrated that at least 2 open reading frames of the *S. avermitilis* bkd gene cluster (E1-alpha [bkdA] and E1-beta [bkdB]) were fully translatable when expressed in *E. coli*. In addition, enzymatic assays aimed to analyze specifically the E1 component of the BCKDH complex confirmed conclusively that two of the recombinant *E. coli* clones, one carrying the whole bkd gene cluster and other carrying together the E1-alpha and the E1-beta ORFs, contained E1 BCKDH-specific enzyme activity.

The present invention relates to the molecular cloning and analysis of a second cluster of novel genes encoding branched-chain alpha-ketoacid dehydrogenase (BCKDH) of *Streptomyces avermitilis*. The cluster contains at least 3 genes (bkdF, bkdG, and bkdH) encoding, respectively, for the E1-alpha, E1-beta and E2 subunits of the *S. avermitilis* BCKDH complex. The bkd gene cluster disclosed here is located approximately 12 kilobases (kb) downstream of the first bkd cluster (bkdA, bkdB, and bkdC genes) recently reported (Denoya, C. D., 1993, U.S. patent application Ser. No. 08/100,518, filed Jul. 30, 1993). Both clusters share a similar gene organization, and they are oriented in the same direction on the *S. avermitilis* chromosome. The corresponding structural genes in both clusters, though highly homologous, are different.

In addition, this invention also relates to the construction of a bkd mutant by genetic engineering technology. The bkd mutant, which carries a chromosomal deletion affecting the bkdF gene, lacks branched-chain alpha-ketoacid dehydrogenase activity, is unable to grow on isoleucine, leucine, and valine as sole carbon sources, and is also incapable of making natural avermectins in a medium lacking both S-2-methylbutyric and isobutyric acids. The mutant disclosed here is useful to produce novel (non-natural) avermectins through fermentation in a medium containing an appropriate alternative carboxylic acid, such as cyclohexane carboxylic acid (CHC). Further, this invention relates to the construction of a mutant that carries a chromosomal deletion affecting both the bkdF gene and the bkdABC gene cluster.

Streptomyces has one major genetic linkage group, one chromosome, that is frequently present in multiple copies per hyphal compartment but is present only as a single copy in the spores. The Streptomyces genome is characteristically large among prokaryotes ($5 \times 10^3$ to $7 \times 10^3$ kilobases [kb]) (Gladek, A., and Zakrzewska, J., 1984, *FEMS Microbiol. Lett.*, 24:73–76), about two times the size of that of *E. coli*.

One particularly interesting aspect of the Streptomyces genetics is the frequent chromosomal rearrangements involving extensive deletions which are frequently accompanied by intense DNA amplifications (Birch A. et al., 1990, *J. Bacteriol.*, 172:4138–4142). Amplifications and deletion events in Streptomyces are two to three orders of magnitude larger than similar events in *E. coli* and *B. subtilis*. Deletions constituting 18% of the chromosome and amplifications representing 45% of the genome have been reported. Despite their inherent long term instability, duplications of certain genes arise with frequencies as high as one in $10^4$ cells. Such duplications are usually generated by illegitimate crossing-over events that involve short, partially homologous sections of DNA in dividing daughter chromosomes. Such duplication events, by creating new stretches of DNA on the same chromosome, automatically tend to be followed by further gene amplification or elimination events. Multiple copies not only of the same gene but also of two different genes with highly similar structures will tend to recombine and to produce deletions. A gene's inherent stability thus demands that it not be too similar to any other genes.

The presence of multiple copies of a gene or group of genes in Streptomyces is not unusual. A modular organization of genes required for synthesis of the polyketide portion of the macrolide antibiotic erythromycin in *Saccharopolyspora erythraea* has been reported (Donadio et al., 1991, *Science*, 252:675–679).

We have discovered that *Streptomyces avermitilis* has at least 2 clusters of bkd genes: one cluster comprising bkdA, bkdB, and bkdC genes, the other cluster comprising bkdF, bkdG, and bkdH genes. We speculate that both the bkdABC (disclosed previously in U.S. patent application Ser. No. 08/100,518, filed Jul. 30, 1993 and referred to above) and the bkdFGH gene clusters disclosed here arose by gene duplication in *S. avermitilis*, and that the 2 copies accumulated, through mutations, enough differences to assure survival (avoiding recombination/deletion events).

In addition to disclosing a second novel cluster of genes encoding BCKDH, we also disclose the construction of a *Streptomyces avermitilis* bkdF mutant by genetic engineering technology. The bkdF mutant lacks branched-chain alpha-ketoacid dehydrogenase activity, is unable to grow with isoleucine, leucine, and valine as sole carbon sources, and is also incapable of making natural avermectins in a medium lacking both S-2-methylbutyric and isobutyric acid. The bkdF mutant is useful for producing novel avermectins through fermentation in a medium containing an appropriate alternative carboxylic acid, such as cyclohexane carboxylic acid (CHC). We also disclose the construction of a mutant that carries a chromosomal deletion affecting both the bkdF gene and the bkdABC gene cluster.

Generation of Streptomycetes mutants using chemical and physical mutagens is an important technology to analyze gene function and regulation, and to develop improved industrial strains. Recent developments in Streptomyces gene cloning have resulted in the possibility of manipulating by recombinant DNA technology a myriad of cloned genes such as resistance, biosynthetic, and regulatory genes, and to elucidate gene organization and regulation. Another mutagenic approach, gene replacement, was successfully applied in *Saccharomyces cerevisiae*, *Escherichia coli*, and *Bacillus subtilis* (Scherer, S. and R. W. Davis, 1979, *Proc. Natl. Acad. Sci. U.S.A.*, 76: 4951–4955; Shortle, D., et al., 1982, *Science*, 217:371–373; Stahl, M. L., and Ferrari, E., 1984, *J. Bacteriol.*, 158:411–418), and also in *Saccharopolyspora erythraea* (Weber, J. M., and Losick, R., 1988, *Gene*, 68:173–180) and several streptomycetes species. This technique allows the introduction of an in vitro generated mutation carried on a plasmid into the chromosome of the host strain. This approach is based on the findings that recombination occurs between the host chromosome and a plasmid containing a homologous region.

Gene replacement in *S. avermitilis* occurs by means of homologous recombination between cloned sequences carried in the vector and their chromosomal counterparts. Presumably, two crossovers occurring simultaneously, or a single crossover leading to integration and a subsequent resolution step where the integrated plasmid is excised, cause reciprocal exchange between the cloned and resident sequences. We have observed both double and single crossover events in *S. avermitilis*. Both mechanisms, double crossover and single crossover, followed by excision result in the same product. By using this approach we were able to disrupt the E1-alpha open reading frame of the bkdF gene of *S. avermitilis*. The disruption involved a chromosomal deletion of about 1.4 kb affecting the 5'-half of the gene encoding the E1-alpha subunit of the BCKDH complex. The resulting mutant strain, which exhibits all the characteristic phenotypical traits of a bkd mutant, is stable and can be used to generate valuable novel avermectins by fermentation.

All publications cited in this document are incorporated herein by reference in their entireties.

Glossary

Technical terms used throughout this application are well known to those skilled in the art of molecular genetics. Terms frequently utilized in this invention are defined below:

Amplification: Refers to the production of additional copies of a chromosomal sequence, found as either intrachromosomal or extrachromosomal DNA.

Antibiotic Resistance Gene: DNA sequence that conveys resistance to an antibiotic when introduced into a host cell that is naturally sensitive to that particular antibiotic. Also known as antibiotic marker.

Clone: Large number of cells or molecules identical with a single ancestor.

Cloning Vector: Any plasmid into which a foreign DNA may be inserted to be cloned. It carries foreign DNA into a host bacterial cell upon transformation.

CoA: Coenzyme A.

Cohesive End Sequence (Cos): DNA sequence derived from bacteriophage lambda allowing in vitro packaging.

Cosmid: Plasmid into which bacteriophage lambda cos sites have been inserted; as a result, the plasmid DNA (carrying foreign DNA inserts) can be packaged in vitro in the phage coat.

cRNA: Single-stranded RNA complementary to DNA, synthesized from the latter by in vitro transcription.

Crossover: Refers to the point where a reciprocal exchange of material between a cloned sequence and its chromosomal counterpart occurs.

Dalton: unit of mass commonly used in connection with molecular dimensions corresponding to one hydrogen atom.

DNA Ligation: The formation of a chemical bond linking two fragments of DNA.

Double Crossover Events: Two crossovers occurring either simultaneously or in succession. As a result, a reciprocal exchange between the cloned and resident sequences occurs.

Gene Cluster: A group of genes physically close on the chromosome.

Gene Replacement: Technique which permits the introduction of an in vitro derived mutation carried on a plasmid into the chromosome. The replacement occurs when the host chromosome and a plasmid containing a region homologous to it recombine.

Genome: Entire chromosome set. The sum total of all of an individual's genes.

Hybridization, Colony Hybridization: Technique used to identify bacterial colonies carrying chimeric vectors whose inserted DNA is similar to some particular sequence.

Hypha: The principal element of the growing or vegetative form of a mold. Hyphae are tubular structures, about 2 to 10 microns in diameter, that form a mass of intertwining strands called mycelium.

kb: Abbreviation for 1,000 base pairs of DNA or RNA.

Linker: Short synthetic duplex oligodeoxynucleotide containing the target site for one or more restriction enzymes. It is added to a vector to create a novel polylinker or multiple cloning site (MCS).

NADH: Reduced nicotinamide adenine dinucleotide.

Nucleotide: building block, or monomeric unit, of nucleic acids.

Oligonucleotide: A short chain of nucleotides.

Operon: A complete unit of bacterial gene expression and regulation, including structural genes, regulator genes, and control elements in DNA recognized by regulator gene product(s).

Plasmid: Autonomous, self-replicating, extrachromosomal circular DNA.

Plasmid Copy Number: Number of plasmid molecules maintained in bacteria for every host chromosome.

Primer: Short sequence of DNA or RNA that is paired to one strand of DNA and provides a free 3'-hydroxy end at which a DNA polymerase starts synthesis of a deoxyribonucleotide chain.

Prokaryotic Cells: The small, relatively simple cells comprising most microorganisms.

Promoter: Region of DNA responsible for the initiation of transcription.

Restriction Enzyme: Enzyme that recognizes a specific short sequence of DNA and cleaves it.

Restriction Recognition Sequence: DNA sequence specifically recognized by a particular restriction enzyme. Also known as target site.

Shuttle Vector: Bifunctional cloning vector able to replicate in one or more alternative hosts (e.g., *E. coli* and Streptomyces).

Single Crossover Event: Single reciprocal genetic recombination occurring at a single point. It causes integration of an incoming circular plasmid or phage vector and a duplication in the homologous chromosome sequence.

Southern Blotting: The procedure for transferring denatured DNA from an agarose gel to a nitrocellulose filter where it can be hybridized with a complementary nucleic acid probe.

Subcloning: Transferring cloned fragments of DNA from one type of vector to another, for example, from a recombinant cosmid to a plasmid. The new recombinant plasmid is then transformed into an appropriate host cell to produce a subclone strain.

Transformation of Bacterial Cells: Describes the acquisition of new genetic markers by incorporation of added DNA.

SUMMARY OF THE INVENTION

This invention relates to an isolated DNA segment that encodes for a branched-chain alpha-ketoacid dehydrogenase complex of an organism belonging to the genus Streptomyces.

This invention also relates to an isolated DNA segment, as described above, that further comprises a DNA region that regulates the expression of such branched-chain alpha-ketoacid dehydrogenase complex.

This invention also relates to an isolated DNA segment that encodes for a *Streptomyces avermitilis* branched-chain alpha-ketoacid dehydrogenase complex.

This invention also relates to a DNA segment comprising the DNA sequence of SEQUENCE ID NO. 1, SEQUENCE ID NO. 2, SEQUENCE ID NO. 3 or SEQUENCE ID NO. 4, as described below, or an allelic variation of such sequence. It also relates to a DNA segment that is a subset of the foregoing DNA segment and functionally equivalent to it.

This invention also relates to: (a) recombinant DNA comprising the DNA sequence of SEQUENCE ID NO. 1, SEQUENCE ID NO. 2, SEQUENCE ID NO. 3 or SEQUENCE ID NO. 4, or an allelic variation of such sequence; (b) a plasmid comprising such recombinant DNA; and (c) a host cell into which such recombinant DNA has been incorporated.

This invention also relates to the genes for branched-chain alpha-ketoacid dehydrogenase complex contained in a DNA segment selected from the group consisting of pCD713, pCD740, pCD747 and pCD854, as defined below.

This invention also relates to a DNA segment comprising the DNA sequence of SEQUENCE ID NO. 1, SEQUENCE ID NO. 2, SEQUENCE ID NO. 3 or SEQUENCE ID NO. 4, or an allelic variation of such sequence.

This invention also relates to a DNA segment comprising a DNA sequence that is a subset of the DNA sequence of SEQUENCE ID NO. 1, SEQUENCE ID NO. 2, SEQUENCE ID NO. 3 or SEQUENCE ID NO. 4, or an allelic variation thereof, and that is capable of hybridizing to, respectively, SEQUENCE ID NO. 1, SEQUENCE ID NO. 2, SEQUENCE ID NO. 3 or SEQUENCE ID NO. 4, or an allelic variation thereof, when used as a probe, or of amplifying all or part of such sequence when used as a polymerase chain reaction primer.

This invention also relates to a substantially purified polypeptide comprising the amino acid sequence of SEQUENCE ID NO. 5, SEQUENCE ID NO. 6, SEQUENCE ID NO. 7 or SEQUENCE ID NO. 8.

This invention also relates to a method of producing a natural avermectin, comprising fermenting, under conditions and in a fermentation medium suitable for producing such natural avermectin, *S. avermitilis* in which the copy number of a genomic fragment comprising one or more of the bkdF, bkdG and bkdH genes has been increased.

This invention relates to a method of producing a natural avermectin, comprising fermenting, under conditions and in a fermentation medium suitable for producing such natural avermectin, *S. avermitilis* in which expression of a genomic fragment comprising one or more of the bkdF, bkdG and bkdH genes has been enhanced by manipulation or replacement of the genes responsible for regulating such expression.

This invention also relates to a method of producing a novel avermectin, comprising fermenting, under conditions and in a fermentation medium suitable for producing such novel avermectin, *S. avermitilis* in which expression of a genomic fragment comprising one or more of the bkdF, bkdG and bkdH genes has been decreased or eliminated by deletion, inactivation, replacement or other manipulation of the genes responsible for such expression.

A preferred embodiment of the invention relates to the foregoing method of producing a novel avermectin, which comprises fermenting, under conditions and in a fermentation medium suitable for producing such novel avermectin, S. *avermitilis* in which a genomic fragment comprising one or more of the bkdF, bkdG, and bkdH genes has been deleted or inactivated.

This invention also relates to a method of producing a novel avermectin, comprising fermenting, under conditions and in a fermentation medium suitable for producing such novel avermectin, S. *avermitilis* in which expression of a genomic fragment comprising one or more of the bkdA, bkdB and bkdC genes and one or more of the bkdF, bkdG and bkdH genes has been decreased or eliminated by deletion, inactivation, replacement or other manipulation of the genes responsible for such expression.

A preferred embodiment of the invention relates to the foregoing method of producing a novel avermectin, which comprises fermenting, under conditions and in an fermentation medium suitable for producing such novel avermectin, S. *avermitilis* in which a genomic fragment comprising one or more of the bkdA, bkdB and bkdC genes and one or more of the bkdF, bkdG and bkdH genes has been deleted or inactivated.

BRIEF DESCRIPTION OF THE DRAWINGS

FIG. 1: The nucleotide sequence of the polymerase chain reaction (PCR) primers utilized to clone a fragment of the S. *avermitilis* bkdF gene (E1-alpha BCKDH). Each primer was designed upon a 9-amino acid long conserved region. The codons corresponding to each conserved amino acid are indicated above the corresponding DNA sequence. The rightward primer was designed upon a region encompassing amino acids 192-200 of the human E1-alpha BCKDH subunit, which was used as a representative model of an E1-alpha BCKDH subunit. The leftward primer was designed upon a region encompassing amino acids 286-293 of the E1-alpha BCKDH subunit. At the 5'-end of the rightward primer there are two extra adenine-containing nucleotides, and two restriction enzyme recognition sequences (EcoRI and SacI) added to facilitate the cloning of the PCR products. Similarly, at the 5'-end of the leftward primer there are two extra adenine-containing nucleotides, and two restriction enzyme recognition sequences (BamHI and XbaI).

FIG. 3: Nucleotide sequence and deduced translation products of the 501-bp S. *avermitilis* genomic DNA fragment (CD613) cloned by PCR using the primers shown in FIG. 1. This genomic fragment contains part of the bkdF gene (E1-alpha BCKDH). Nucleotides are numbered at the top of the sequence lines. The deduced amino acid sequence is shown below the corresponding codon sequence.

FIG. 4: Nucleotide sequence and deduced translation products of the 201-bp S. *avermitilis* genomic DNA region sequenced from the PstI end of the pCD746 subclone using the SP6 vector primer. The deduced translation product represents part of the E1-beta component of the BCKDH complex corresponding to the bkdG gene. Nucleotides are numbered at the top of the sequence lines. The deduced amino acid sequence is shown below the corresponding codon sequence.

FIG. 5: Nucleotide sequence (sequence CD785) and deduced translation products of the 194-bp S. *avermitilis* genomic DNA region sequenced from both ends of the mini-gamma-delta-1 insertion "A3" located approximately 1.7 kb from the BamHI end containing the bkdF gene in the 4.1 kb BamHI genomic fragment. The deduced translation product represents the C-terminal end of the E1-beta component of the BCKDH complex corresponding to the bkdG gene. Nucleotides are numbered at the top of the sequence lines. The deduced amino acid sequence is shown below the corresponding codon sequence.

FIG. 6: Nucleotide sequence (sequence CD786) and deduced translation products of the 455-bp S. *avermitilis* genomic DNA region sequenced from both ends of the mini-gamma-delta-1 insertion "A5" located approximately 3 kb from the BamHI end containing the bkdF gene in the 4.1 kb BamHI genomic fragment. The deduced translation product represents the C-terminal end of the E2 component of the BCKDH complex corresponding to the bkdH gene. Nucleotides are numbered at the top of the sequence lines. The deduced amino acid sequence is shown below the corresponding codon sequence.

DETAILED DESCRIPTION OF THE INVENTION

The novel DNA sequences of this invention were cloned using a combination of two molecular genetics techniques, DNA polymerase chain reaction (PCR) and homology probing.

The procedures for identifying and cloning the novel DNA sequences of this invention and the construction of a bkd mutant by gene replacement are described below.

Figure 2:
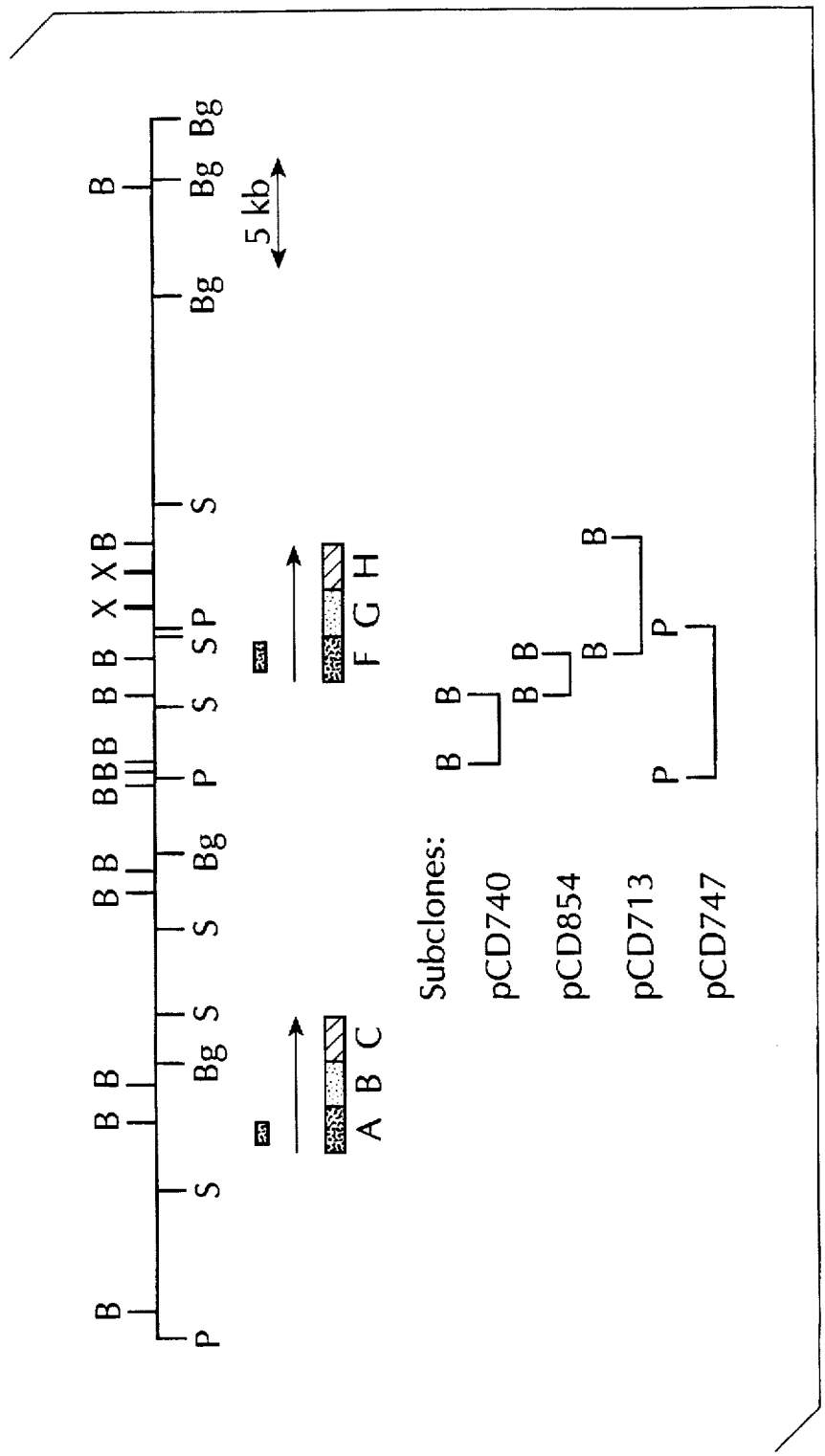
FIG. 2: Genomic restriction map, location and subclones for the *Streptomyces avermitilis* bkdFGH gene cluster. Also indicated is the location of the bkdABC gene cluster previously disclosed (see Denoya, C. D., U.S. patent application Ser. No. 08/100,518, referred to above). The black boxes below the map indicate the location and orientation of the initial E1-alpha-specific S. *avermitilis* genomic fragments cloned using PCR. Genomic subclones (derivatives of pGEM-3Z) are indicated. The location and organization of the bkdF, bkdG, and bkdH structural genes encoding E1-alpha, E1-beta, and E2 BCKDH subunits, respectively, are also indicated. Polarity of identified open reading frames (denoted by boxes) is left to right. Abbreviations: B, BamHI; Bg, BglII; P, PstI; and S, SphI. "X" denotes the location of a transposon mini-gamma-delta-1 insertion used to sequence DNA regions located downstream of the bkdF open reading frame, as described below.

First, 2 PCR primers, named "Rightward" and "Leftward" (FIG. 1), were designed upon conserved regions identified from a multiple alignment of deduced E1-alpha BCKDH peptide sequences from various species and available from the literature. A PCR product, approximately 0.55 kb long, was detected by PCR amplification of S. avermitilis genomic DNA using both the rightward and the leftward primers. That PCR-amplified DNA fragment was subsequently cloned into the E. coli vector pGEM-3Z to produce recombinant plasmid pCD613. Subsequently, plasmid pCD613 was transformed into E. coli DH5-alpha competent cells. One transformant was selected and designated as strain CD613. DNA sequencing of cloned DNA fragment CD613 showed the existence of an open reading frame with a deduced peptide highly homologous to E1-alpha BCKDH subunit (FIG. 3). Cloned CD613 genomic DNA fragment was then used as a probe to screen a S. avermitilis chromosomal library by colony hybridization. Several cosmid clones were identified. Restriction and Southern blot analyses showed that all the selected cosmids clones carried overlapping genomic fragments. DNA sequencing of the chromosomal region, obtained from subcloned genomic DNA fragments (as fully described in Example 6), demonstrated that sequence CD613 was part of a complete bkd gene cluster. Cloned S. avermitilis bkd genes encompass a region of the chromosome approximately 4 kilobases in length (FIG. 2). DNA sequence analysis showed the presence of bkd structural genes arranged as a cluster organized as follows: E1-alpha (bkdF), E1-beta (bkdG), and E2 (bkdH) open reading frames (FIGS. 2–6).

Next, a plasmid carrying an inactivated version of the bkdF gene was constructed. As shown in FIG. 2, three adjacent BamHI restriction fragments in the S. avermitilis chromosome were mapped (from left to right): 2.3 kb, 1.4 kb and 4.1 kb. The 1.4 kb BamHI genomic fragment carries the beginning of the E1-alpha open reading frame (ORF-1) (gene bkdF). The 4.1 kb BamHI carries the rest of the bkd gene cluster (end of bkdF, bkdG, and bkdH). Plasmid pCD768 is a derivative of shuttle vector pCD262 carrying two S. avermitilis genomic fragments (2.3 and 4.1 kb BamHI) which are adjacent on each side of the 1.4 kb BamHI fragment of the chromosome. In addition, pCD768 carries the ermE marker located between the 2.3 and the 4.1 kb BamHI fragments. The ermE marker (which confers resistance to erythromycin) lies in the opposite orientation to that of the ORF-1 (bkdF), to avoid possible difficulties caused by overexpression of downstream genes. This construct produced a 1.4 kb deletion (ORF1 will be affected) in the host genome upon recombination, as described below.

Plasmid pCD768 was transformed into S. avermitilis 31272 SC2 host protoplasts. Two transformants showing resistance to both erythromycin (erm-R) and thiostrepton (tsr-R) antibiotics were selected. Transformant No. 1 (CD783) was grown in liquid medium and protoplasts were prepared and plated on agar medium containing erythromycin. Fifty clones were selected and further analyzed: 46 were erm-R, tsr-R; 4 were erm-R, tsr-S. The latter four clones exhibited a bkd-deficient phenotype, as follows: they were unable to grow on ILV minimal medium plates; they had no detectable E1 (branched-chain decarboxylase) activity; and, upon fermentation, they were unable to synthesize natural avermectins unless supplemented with either S(+)-2-methylbutyric acid or isobutyric acid (see Example 9). In addition, when CHC was added to the fermentation medium, novel avermectins (CHC-avermectins) were synthesized, demonstrating that the bkd block did not affect the avermectin biosynthetic cellular machinery. One clone out of this group of 4 (clone pp15) was formally named *S. avermitilis* strain CD794 and is being deposited in the American Type Culture Collection as an exemplification of this invention. Finally, Southern hybridization analysis confirmed that ORF-1 corresponding to the bkdF gene was disrupted as expected upon gene replacement in *S. avermitilis* ATCC 31272 SC2.

A full description of the experimental steps involved in the cloning of the *S. avermitilis* bkd genes, and results obtained, follows:

(a) Identification of conserved regions in the E1-alpha BCKDH peptide subunit that could serve as candidate sites for binding of PCR primers.

Four E1-alpha BCKDH peptide sequences from human (Fisher et al., 1989, *J. Biol. Chem.*, 264:3448–3453), rat (Zhang et al., 1987, *J. Biol. Chem.*, 262:15220–15224), *Pseudomonas putida* (Sokatch et al., 1988, *Eur. J. Biochem.*, 176:311–317), and *Bacillus stearothermophilus* (Perham et al., 1990, *Eur. J. Biochem.*, 191:337–346) were aligned to identify conserved regions that could serve as sequences to design corresponding PCR primers. Computer analysis to identify regions of the E1-alpha subunit that are highly conserved in both prokaryotic and eukaryotic BCKDH complexes was done using the LineUp and Pretty programs from the GCG sequence analysis software package (GCG, Madison, Wis.). Multiple alignment of the four E1alpha BCKDH peptides showed several regions of extended homology (see Wexler, I. D. et al., 1991, *FEBS Letters*, 282:209–213). The thiamin pyrophosphate binding motif (Perham et al., 1989, *FEBS Letters*, 255:77–82) located between human E1-alpha amino acids 182–229, and a region encompassing phosphorylation sites 1 and 2, spanning amino acids 291–307 were notably conserved in all four E1-alpha BCKDH peptides analyzed. Also present was a previously described region of high homology located between amino acids 245–289. This region appears to be unique to alpha-ketoacid dehydrogenases which have both alpha and beta subunits, and is not homologous to any sequence in *E. coli* PDH E1 or the E1 components of *E. coli* and yeast alpha-ketoglutarate dehydrogenase complexes, which are dimers composed of only a single E1 polypeptide. For the above mentioned reasons, the latter region of homology has been suggested to play a role in subunit interaction (Patel et al., 1991, *FEBS Letters*, 282:209–213). Conserved regions chosen for PCR primer design encoded amino acid residues 192 to 200, and 286 to 293 of the human E1-alpha BCKDH protein.

(b) Design of novel oligonucleotides derived upon those E1-alpha BCKDH conserved regions to be used as PCR primers.

As previously discussed, two conserved regions of the E1-alpha BCKDH subunit were selected from the multiple alignment study. The Rightward PCR primer (FIG. 1) was designed upon a region encompassing amino acids 192–200 of the human E1-alpha BCKDH subunit, which was used as a representative model of an E1-alpha BCKDH subunit. These amino acids are located within the thiamin pyrophosphate binding motif. The Leftward PCR primer (FIG. 1) was designed upon a region encompassing amino acids 286–293 of the human E1-alpha BCKDH subunit. The latter amino acid sequence comprises the end part of the subunit interaction site and the beginning of the phosphorylation site conserved regions. Streptomyces gene codon assignments were used (F. Wright and M. J. Bibb, 1992, *Gene*, 113:55–65). At the 5'-end of the Rightward primer there were two extra adenine-containing nucleotides, and two restriction enzyme recognition sequences (EcoRI and SacI) to facilitate the cloning of the PCR products. Similarly, at the 5' end of the Leftward primer there were two extra adenine-containing nucleotides, and two restriction enzyme recognition sequences (BamHI and XbaI).

The complete sequence of the Rightward PCR primer is:

5'-AA<u>GAATTC</u><u>GAGCTC</u>GGCGACGGCGCCACCTCCGA GGGCGAC-3' (SEQ ID NO: 9).

The complete sequence of the Leftward PCR primer is:

5'-AA<u>GGATCC</u><u>TCTAGA</u>GGTSSWGTGGKGGCCGATS CGGWA-3' (SEQ ID NO: 10).

The International Union of Biochemistry (IUB) rules of nomenclature for nucleotides were used to describe DNA sequences. Redundancies are identified following the IUB Group Codes, as follows: K=G+T, S=G+C, and W=A+T. Restriction recognition sequences not homologous to the E1-alpha bkd genes and incorporated into the primers for cloning purposes are underlined (see FIG. 1).

(c) PCR amplification of *S. avermitilis* genomic DNA fragments.

*S. avermitilis* genomic DNA was enzymatically amplified using reaction conditions appropriate for DNA with a high GC content, allowing efficient and specific amplification of streptomycetes DNA (see Example 2). PCR was performed using the primer combination described above (Rightward primer, 5'-AAGAATTCGAGCTCGGCGACGGCGCCA CCTCCGAGGGCGAC-3'(SEQ ID NO: 9), and Leftward primer, 5'-AAGGATCCTCTAGAGGTSSWGTGGKGGC CGATSCGGWA-3'(SEQ ID NO: 10)). The amplification products were size fractionated by agarose gel electrophoresis. Under the PCR conditions described above, a single DNA band (approximately 550 base pairs long) was detected when using this primer combination.

(d) Cloning of amplified genomic DNA fragment into *Escherichia coli* cloning vector, and subsequent transformation into *E. coli* host.

As mentioned before, an EcoRI restriction site was incorporated into the Rightward PCR primer for cloning convenience, and a XbaI restriction site was present in the 5' end of the Leftward primer. The 0.55 kb PCR fragment was recovered from the agarose gel by electroelution and it was digested with both EcoRI and XbaI restriction enzymes. Many recombinant clones were recovered after ligating the specific fragment into a linearized *E. coli* vector (pGEM-3Z), to produce recombinant plasmid pCD613, and transforming it into *E. coli* competent cells. One transformant was selected for further characterization and it was designated as strain CD613. Confirming restriction analysis showed that plasmid pCD613, isolated from *E. coli* strain CD613, indeed contained the 0.55 kb *S. avermitilis* insert.

(e) DNA sequencing of cloned fragment and identification of bkd-specific sequences.

The 0.55 kb insert present in plasmid pCD613 was sequenced by a double-stranded sequencing procedure using a pair of vector primers (see Example 6A). In addition, a 0.35 kb SalI fragment, which is located internally in the 0.55 kb PCR insert, was subcloned into bacteriophage M13, and was sequenced by a single-stranded sequencing protocol (see Example 6B). DNA sequencing was performed by the dideoxynucleotide-chain termination method, with a single-stranded DNA template and the TaqTrack kit (Promega). Codon preference analysis (GCG sequence analysis software package, Madison, Wis.) of the DNA sequencing data showed the existence of an open reading frame having the expected codon usage for a streptomycetes gene.

Next, the putative open reading frame was translated into an amino sequence using the Seq and Translate programs of the IntelliGenetics Suite software (IntelliGenetics Inc., Mountain View, Calif.). Finally, data bank similarity searches with the query peptide sequence were run using the FASTDB program of the IntelliGenetics software. All data bank searches, searching either DNA data banks (GenBank®, National Institute of Health, and European Molecular Biology Laboratory (EMBL), Heidelberg, Germany) or protein data banks (PIR and Swiss-Prot), unequivocally showed that the sequence derived from clone CD613 was highly homologous but novel and distinct from all other E1-alpha BCKDH peptides listed in the data banks, from both prokaryotic and eukaryotic origin. In addition, the novel *Streptomyces avermitilis* E1-alpha BCKDH peptide sequence encoded by gene bkdA (see Denoya, C. D., 1993, "Cloned genes encoding branched-chain alpha-ketoacid dehydrogenase complex from *Streptomyces avermitilis*", U.S. patent application Ser. No. 08/100,518 filed Jul. 30, 1993) was also compared. From this analysis, it was concluded that the 550 bp *S. avermitilis* genomic PCR product cloned in *E. coli* strain CD613 represents indeed a novel E1-alpha bkd gene fragment.

(f) Cloning of the whole *S. avermitilis* bkd gene cluster, restriction and Southern blot analyses, and construction of chromosomal map.

As described above, the original 0.55 kb PCR fragment contains an internal 0.35 kb SalI fragment. This small fragment was used as a radioactively-labeled probe to screen a *S. avermitilis* genomic DNA cosmid library by colony hybridization. Ten clones were identified and recovered. Restriction and Southern blot hybridization analyses showed that the ten clones contain overlapping sequences originating from the same chromosomal region. The same probe was used at high stringency against Southern blots of digested chromosomal DNA from *S. avermitilis* ATCC 31272 SC2. The latter analysis confirmed the identity of the clones recovered from the genomic library. Surprisingly, two of the cosmid clones hybridized also to a bkdA specific probe (see Denoya, C. D., 1993, "Cloned genes encoding branched-chain alpha-ketoacid dehydrogenase complex from *Streptomyces avermitilis*", U.S. patent application Ser. No. 08/100, 518, filed Jul. 30, 1993) suggesting that the bkd gene described here (named bkdF) may be located near the gene cluster comprising bkdA, bkdB, and bkdC. A restriction map of the genomic region containing the *S. avermitilis* CD613 sequence was constructed (FIG. 2). As predicted from the hybridization data discussed above, the bkdF gene is separated from the bkdABC gene cluster by only 12 kilobases.

(g) Subcloning of genomic DNA fragments derived from cosmid clones and DNA sequencing of the *S. avermitilis* chromosomal region carrying bkd gene cluster.

BamHI and PstI genomic fragments, covering the entire CD613 bkd region of the *S. avermitilis* chromosome, were subcloned from DNA library cosmid clones into the *E. coli* vector pGEM-3Z. A list of the subclones constructed during this work, including a brief description of each plasmid, follows:

1. Plasmid pCD740 contains a 2.3 kb BamHI fragment;
2. Plasmid pCD854 contains a 1.4 kb BamHI fragment;
3. Plasmid pCD713 contains a 4.1 kb BamHI fragment; and
4. Plasmid pCD747 contains an approximately 5 kb PstI insert.

In addition, a subclone containing an approximately 3.1 kb PstI/BamHI fragment was derived from the 4.1 kb BamHI fragment carried in plasmid pCD713. The new construct was recorded as plasmid pCD746 and it was used for DNA sequencing, as described below. Plasmid restriction mapping, Southern hybridization, and PCR analysis confirmed the identity of each subclone.

(h) Computer analysis of DNA sequencing data obtained from cloned DNA fragments and identification of S. avermitilis E1-alpha, E1-beta, and E2 bkd open reading frames.

DNA sequencing data was obtained from a number of different subclones and constructs, as follows:

1. CD613: Represents the original PCR clone described in Sections "c" and "d" above and in the Examples 2 and 3. It contains part of the Open Reading Frame 1 (ORF-1) which corresponds to the bkdF gene encoding the E1-alpha component of the BCKDH complex (FIG. 3).

2. CD746: Represents the 3.1 kb PstI/BamHI fragment derived from pCD713 (see section "g" above). DNA sequencing data, obtained by sequencing the PstI end of the pCD746 insert using the SP6 vector primer (purchased from Promega Co.), revealed part of the ORF-2 which corresponds to the bkdG gene encoding the E1-beta component of the BCKDH complex (FIG. 4).

3. CD785: Transposon mini-gamma-delta-1 insertion used to sequence DNA regions located downstream of the bkdF open reading frame in the cloned 4.1 kb BamHI genomic fragment. This mini-gamma-delta-1 insertion, named "A3", was located approximately 1.7 kb from the BamHI end containing the bkdF gene. DNA sequencing performed from both ends of insertion A3 (see Example 6C) showed the presence of an ORF corresponding to the end of the E1-beta ORF (ORF-2) (bkdG) (FIG. 5).

4. CD786: Transposon mini-gamma-delta-1 insertion used to sequence DNA regions located downstream of the bkdF open reading frame in the cloned 4.1 kb BamHI genomic fragment. This mini-gamma-delta-1 insertion, named "A5", was located approximately 3 kb from the BamHI end containing the bkdF gene. DNA sequencing performed from both ends of insertion A5 (see Example 6C) showed the presence of an ORF corresponding to the end of the E2 ORF (ORF-3) (bkdH) (FIG. 6).

Sliding base composition analysis of the sequenced genomic region containing the S. avermitilis E1-alpha, E1-beta and E2 (partial) bkd open reading frames (ORFs) was performed using the "DNA Inspector" software (Textco, N.H.). This analysis provided a profile of the running average of the G+C content using a stretch length of 30 bases and an offset value of 20. Overall G+C content corresponding to this region of the S. avermitilis chromosome was 69%. The G+C content as a function of codon position was also analyzed. Open reading frames were detected by using the program "CodonPreference" (Genetics Computer Group, Madison, Wis.) with a Streptomyces codon usage table for 64 genes (F. Wright and M. J. Bibb, 1992, Gene, 113:55–65). The CodonPreference program is a frame-specific gene finder that tries to recognize protein coding sequences by virtue of their similarity to a codon frequency table or by the bias of their composition (usually GC) in the third position of each codon. ORFs were shown as boxes beneath the plot for their respective reading frames. All start (ATG) and stop codons were also detected (vertical lines). Rare codons found in each reading frame were marked below each ORF plot. The G+C content was calculated by using a sliding window of 25 codons, so a lag of about 25 codons was expected before the full impact of a protein coding region was observed. Three profiles were obtained, as follows: 1, First position in triplet; 2, second position in triplet; 3, third position in triplet. As a result of this analysis, three bkd ORFs were located, corresponding to the following BCKDH subunits: E1-alpha, E1-beta, and E2.

(i) Construction of a S. avermitilis bkd mutant.

The technique used for introducing the deletion is a variation of the gene replacement methods used in Saccharomyces cerevisiae, Escherichia coli, and Bacillus subtilis (Scherer, S. and R. W. Davis, 1979, Proc. Natl. Acad. Sci. U.S.A., 76:4951–4955; Shortle, D., et al., 1982, Science, 217:371–373; Stahl, M. L., and Ferrari, E., 1984, J. Bacteriol., 158:411–418). A general description of this technology, specifically applied to Streptomyces, can be found in the review paper "Genetic Manipulation of Streptomyces: Integrating Vectors and Gene Replacement", by Kieser, T., and Hopwood, D. A. (1991, Methods in Enzymology, vol. 204, 430–458). Furthermore, a detailed description of this technique, including an additional protoplasting step, necessary to assure single colony isolates and to increase the frequency of plasmid elimination, can be found in the paper by Anzai et al., entitled "Replacement of Streptomyces hygroscopicus genomic segments with in vitro altered DNA sequences", Journal of Antibiotics, 1988, vol. XLI, No. 2, pp. 226–233.

A crucial step to the development of a mutated industrial strain by gene replacement is the construction of an integration vector that will work efficiently in that particular strain. In addition, when replacing genes in the Streptomyces chromosome, one of the major problems is elimination of the vector. Escherichia coli plasmids with selectable markers for Streptomyces might seem ideal because they cannot replicate in Streptomyces. E. coli plasmids have been used successfully in S. ambofaciens and S. lividans (Kieser, T., and Hopwood, D. A., 1991, Genetic Manipulation of Streptomyces: Integrating Vectors and Gene Replacement, in: Methods in Enzymology, vol. 204, 430–458). However, in our experience this strategy showed a low efficiency of integration in S. avermitilis, resulting mostly in single crossover events.

We have recently developed a number of versatile shuttle vectors useful for cloning both in Streptomyces and in E. coli, and for a variety of applications in molecular genetics technology in Streptomyces (C. D. Denoya, 1993, "Novel Bacterial Plasmid Shuttle Vectors for Streptomyces sp. and Escherichia coli", U.S. patent application Ser. No. 032,925, filed Mar. 18, 1993). These shuttles are structurally stable and replicate efficiently in E. coli and in a number of Streptomyces species, allowing transfer of a wide size range of cloned DNA fragments back and forth from one host to another. Three of the shuttle vectors (pCD262, pCD385, and pCD500) carry a Streptomyces temperature sensitive origin of replication that controls for a moderate-to-high copy number in Streptomyces. The temperature sensitivity of this replicon allows its application in Streptomyces gene replacement and mutant design experiments.

Shuttle vectors pCD262 and pCD500 were successfully employed in the construction of the bkd-deficient strain described here. This vector is stably maintained as an autonomously replicating, high copy number plasmids in S. avermitilis. However, when a strain of S. avermitilis that has been transformed with any of these vectors is submitted to stress conditions, such as high temperature, sporulation, or protoplasting and regeneration, numerous plasmid-free colonies can be recovered. We have taken advantage of this characteristic to use either pCD262 or pCD500 as an integration vector in gene disruption experiments in *S. avermitilis.*

The mechanism of the gene replacement in *S. avermitilis* is presumably a double crossover or a single crossover leading to integration and a subsequent resolution step where the integrated plasmid is excised. We have observed both double and single crossover events in *S. avermitilis.* Both mechanisms, double crossover and single crossover, followed by excision, result in the same product. By using this approach we were able to disrupt the E1-alpha open reading frame corresponding to the bkdF gene of the *S. avermitilis* bkd gene cluster described here. The disruption involved a chromosomal deletion of about 1.4 kb affecting the 5'-half of the gene encoding the E1-alpha subunit of the BCKDH complex. The resulting mutant strain, which exhibits all the characteristic phenotypical traits of a bkd mutant, is stable and can be used to generate valuable novel avermectin products by fermentation.

Figure 7:
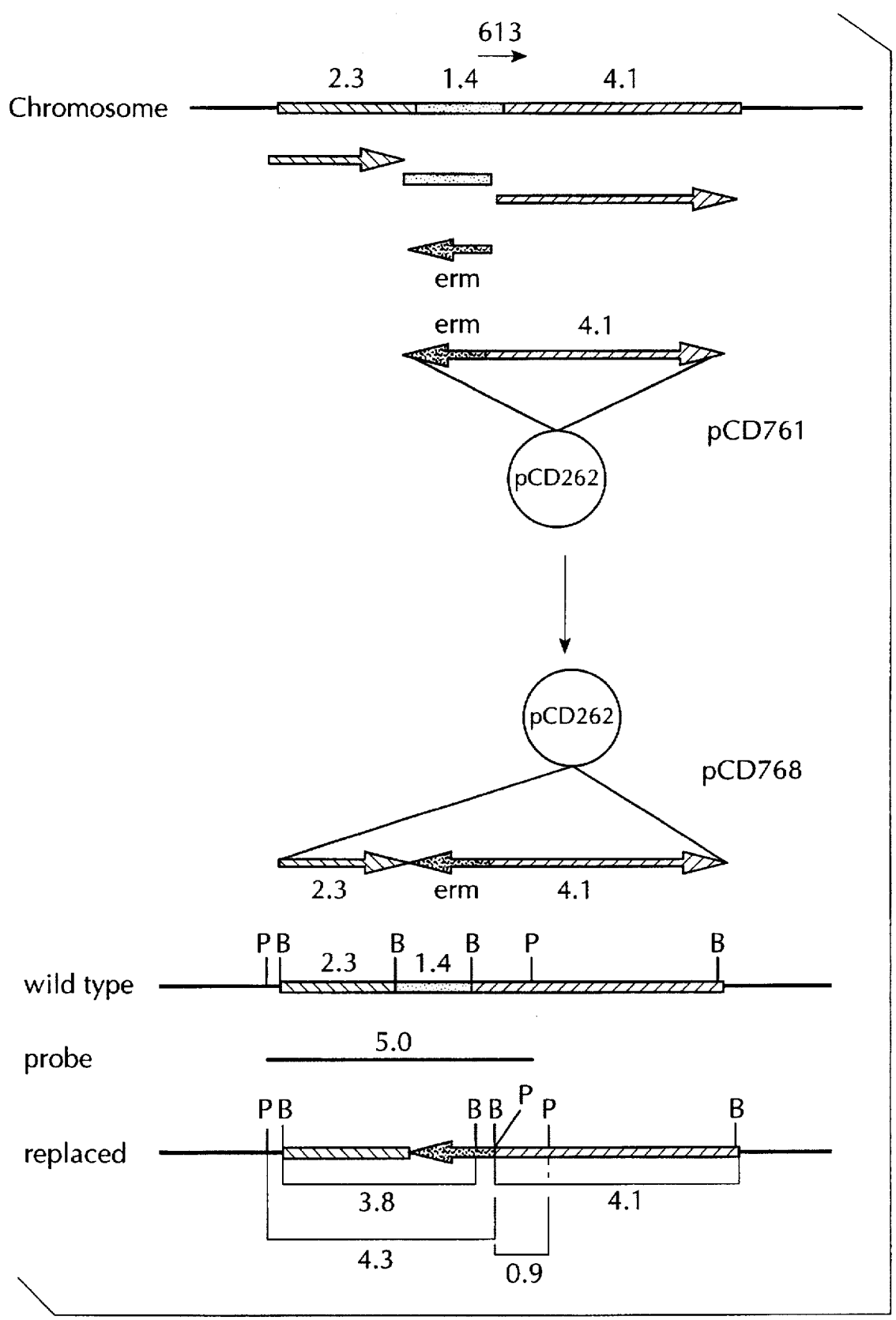
FIG. 7: Construction of the gene replacement vector pCD768 and genomic restriction map of the S. *avermitilis* bkdF mutant strain CD794. Plasmid pCD768 is a derivative of shuttle vector pCD262 carrying the 2.3 and the 4.1 kb BamHI S. *avermitilis* genomic fragments flanking the ermE marker (black arrow). Plasmid pCD761 is an intermediate construct, as described below. Genomic restriction maps (wild type and replaced strains) of the region of the S. *avermitilis* chromosome containing the bkdF gene are also shown. These maps were deduced from Southern hybridization analysis using the 5.0 kb PstI genomic fragment as a probe. Abbreviations: B, BamHI; P, PstI. Numbers above each DNA fragment indicate length in kilobases (kb).

More specifically, we constructed a bkdF mutant by replacing a segment of the E1-alpha BCKDH gene (bkdF) in the *S. avermitilis* ATCC 31272 SC2 chromosome with the ermE gene (for erythromycin resistance) from *Saccharopolyspora erythraea.* As mentioned above, this was achieved by using a novel bifunctional (*E. coli/*Streptomyces) vector (pCD262) that proved to work efficiently in both cloning and gene replacement experiments in *S. avermitilis.* As shown in FIG. 7, three adjacent BamHI restriction fragments in the *S. avermitilis* chromosome were mapped (from left to right): 2.3 kb, 1.4 kb and 4.1 kb. The 1.4 kb BamHI genomic fragment carries the beginning of the E1-alpha open reading frame (ORF-1) (gene bkdF). The 4.1 kb BamHI carries the rest of the bkd gene cluster (end of bkdF, bkdG, and bkdH).

Figure 8:
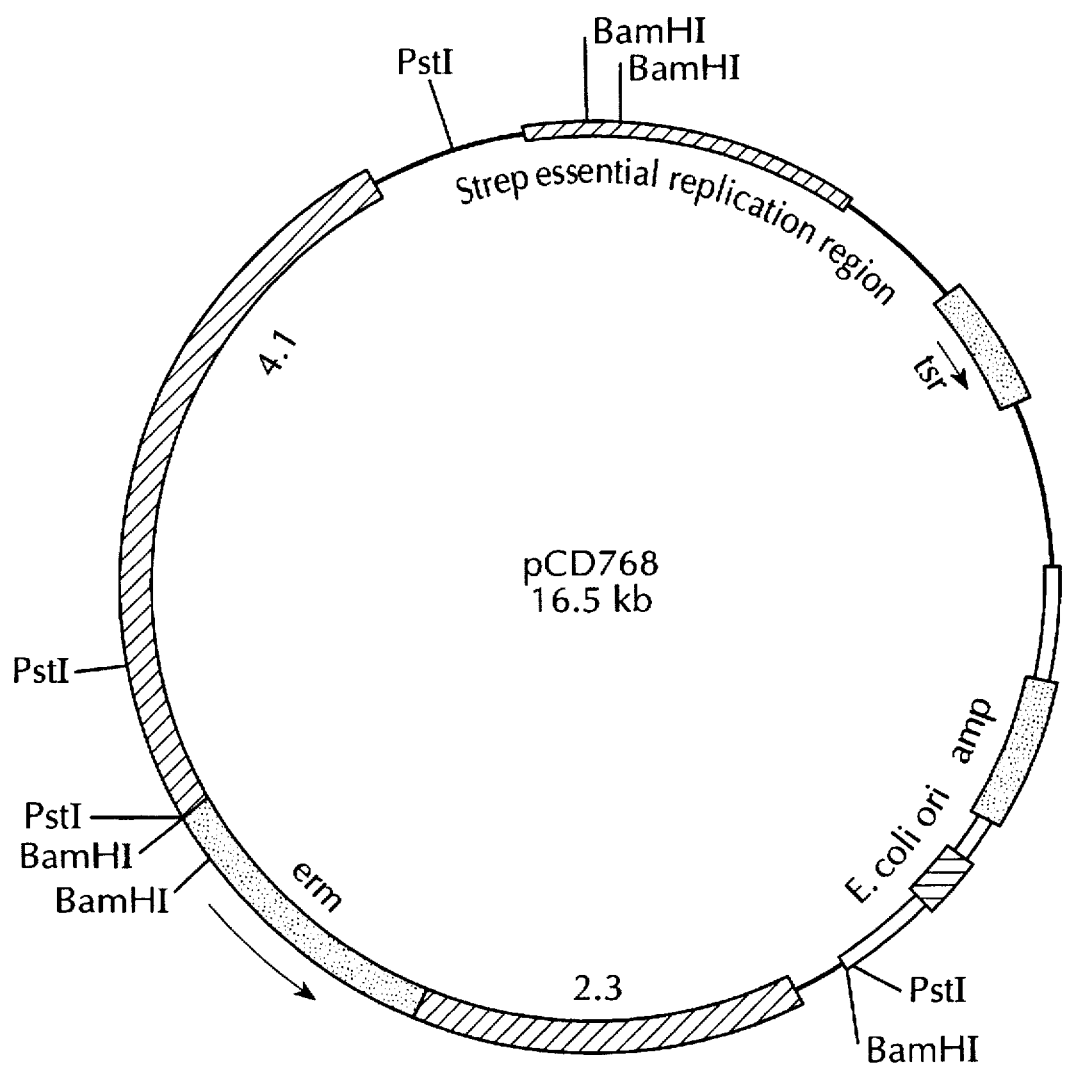
FIG. 8: Restriction map of the gene replacement vector pCD768. Shaded boxes indicate: tsr—thiostrepton resistance marker; amp—ampicillin resistance marker; "2.3"—2.3 kb BamHI S. *avermitilis* genomic fragment; erm—erythromycin resistance marker; "4.1"—4.1 kb BamHI S. *avermitilis* genomic fragment. Streptomyces and E. *coli* origin of replication regions are also indicated. The white boxes indicate the E. *coli* vector region. The arrows indicate the direction of transcription and translation.

Plasmid pCD768 is a derivative of shuttle vector pCD262 carrying two *S. avermitilis* genomic fragments (2.3 and 4.1 kb BamHI) which flank the 1.4 kb BamHI fragment (FIG. 8). In addition, pCD768 carries the ermE marker located between the 2.3 and the 4.1 kb BamHI fragments. The ermE marker lies in the opposite orientation to that of the ORF-1 (bkdF), to avoid possible difficulties caused by overexpression of downstream genes. This construct is expected to produce a 1.4 kb deletion (ORF-1 will be affected) in the host genome upon recombination.

Plasmid pCD768 was transformed into *S. avermitilis* ATCC 31272 SC2 host protoplasts. Two transformants resistant to both erythromycin (erm-R) and thiostrepton (tsr-R) antibiotics were selected (see Example 9). Transformant #1 (CD783) was grown in liquid medium and protoplasts were prepared and plated on agar medium containing erythromycin. Fifty clones were selected and further analyzed: 46 were erm-R, tsr-R; 4 were erm-R, tsr-S (pp15, pp17, pp22, and pp40). Four clones from the latter group as well as 2 clones from the former group (pp14 and pp21, see Table I in Example 9) were further analyzed. All of them exhibited a bkd-deficient phenotype, as follows: All 4 erm-R, tsr-S clones were unable to grow on ILV minimal medium plates; had no activity when assayed for the E1 component of the BCKDH complex; and, upon fermentation, were unable to synthesize natural avermectins unless supplemented with either S(+)-2-methylbutyric acid or isobutyric acid (see Example 9). In addition, when CHC was added to the fermentation medium, novel avermectins (CHC avermectins) were synthesized, demonstrating that the bkd block did not affect the avermectin biosynthetic cellular machinery (see Example 9). One clone out of this group of 4 (clone pp15) was formally named *S. avermitilis* strain CD794 and is being deposited in the American Type Culture Collection as exemplification of this invention. Finally, Southern hybridization analysis clearly confirmed that ORF-1 corresponding to the bkdF gene was disrupted as expected upon gene replacement in *S. avermitilis* ATCC 31272 SC2 (see Example 5).

EXAMPLES

The following are detailed examples of the experimental procedures used to identify, clone and analyze the bkdFGH genes from *S. avermitilis,* which are also illustrated in the accompanying Figures. In addition, the construction of two bkd-deficient mutants by gene replacement are also described. Additional details of standard techniques, which are well known to those skilled in molecular biology, and the designation of the particular enzymes used, are described, for example, in the laboratory manual "Molecular Cloning" by Sambrook et al. (Cold Spring Harbor Laboratory, 1989).

EXAMPLE 1

Preparation of *S. avermitilis* Genomic DNA

*S. avermitilis* ATCC 31272 SC2 (single colony isolate #2) mycelium was grown as a confluent lawn on YPD-2 agar medium for 7 days at 29° C. The medium comprised:

| | |
|---|---|
| Difco Yeast Extract | 10 g |
| Difco Bacto-peptone | 10 g |
| Dextrose | 5 g |
| Difco Bacto agar | 20 g |
| Sodium acetate | 2 g |
| MOPS | 10 g | pH adjusted to 7.0.
Final volume: 1 L.
Autoclaved for 25 minutes at 121° C.

The mycelium was then used to inoculate 30 ml of AS-7 medium (see Hafner et al., 1988, European Patent Application #88300353.5, publication #0 284176) in a 300-ml baffled flask, which was maintained with shaking (230 rpm) at 29° C. for 24 hours. The medium comprised:

| | |
|---|---|
| Thinned starch[1] | 20 g |
| Ardamine pH[2] | 5 g |
| Pharmamedia[3] | 15 g |
| CaCO$_3$ | 2 g | pH adjusted to 7.2 with NaOH.
Final volume: 1 L.
Autoclaved for 25 minutes at 121° C.
[1]Prepared by hydrolysis of starch with "termamyl", an alpha-amylase from *Bacillus licheniformis* available from Novo Enzymes, Wilton CT, to a dextrose equivalent of approximately 40%.
[2]From Yeast Products, Inc., Clifton, NJ 07012.
[3]From Traders Protein, Memphis, TN 38108.

Approximately 0.3 ml of the above culture was used to inoculate another 300-ml baffled flask containing 30 ml of modified liquid Yeast Extract Malt Extract (YEME) medium (Bibb, M. J., Freeman, R. F., and D. A. Hopwood, 1977, *Mol. Gen. Genetics,* 154:155–166). Modified YEME medium contained per liter:

| | |
|---|---|
| Difco Yeast extract | 3 g |
| Difco Bacto-peptone | 5 g |
| Oxoid Malt extract | 3 g |

| Sucrose | 300 g |
| Glucose | 10 g |

Autoclaved for 40 minutes at 121° C.
2 ml of 2.5 M MgCl$_2$.6H$_2$O were added after autoclaving.
Final volume adjusted to 1 L.

Cultures were grown for 48–72 hours at 29° C. Mycelia were recovered by centrifugation and genomic DNA was prepared following the protocol "Isolation of Streptomyces Total DNA by Caesium Chloride Gradient Centrifugation: Procedure 2", as found in the textbook "Genetic Manipulation of Streptomyces, A Laboratory Manual", The John Innes Foundation, Norwich, U.K., 1985, by D. A. Hopwood et al. DNA pellets were resuspended in 3 ml TE buffer (10 mM Tris-HCl, pH 8.0, 1 mM EDTA).

Example 2

Polymerase Chain Reaction of *S. avermitilis* Genomic DNA Amplification

*S. avermitilis* genomic DNA was enzymatically amplified by using a Perkin-Elmer Cetus thermal cycler. The PCR reaction was carried out with Taq polymerase (Perkin-Elmer Cetus) and the buffer provided by the manufacturer in the presence of 200 micromolar dNTP, 0.5 micromolar of each primer, 50 ng of template DNA, and 2.5 units of enzyme in a fined volume of 100 microliters for 30 cycles. The thermal profile of the first cycle was: 95° C. for 3 min (denaturation step), 55° C. for 2 min (annealing step), and 72° C. for 2 min (extension step). The subsequent 29 cycles had a similar thermal profile except that the denaturation step was shortened to 1.5 min. DNA primers were supplied by Genosys Biotechnologies, Inc. (Texas). The Rightward primer (FIG. 1) was 5'-AAGAATTCGAGCTCGGCGACGGCGCCA CCTCCGAGGGCGAC-3'(SEQ ID NO: 9), and the Leftward primer (FIG. 1) was 5'-AAGGATCCTCTAGAGGTSS WGTGGKGGCCGATSCGGWA-3'(SEQ ID NO: 10).

The International Union of Biochemistry (IUB) rules of nomenclature for nucleotides were used to describe DNA sequences. Redundancies are identified following the IUB Group Codes, as follows: K=G+T, S=G+C, and W=A+T. Restriction recognition sequences not homologous to the E1-alpha bkd genes and incorporated into the primers for cloning purposes are underlined (see FIG. 1). The amplification products were size fractionated by agarose gel electrophoresis. The PCR sample was electrophoresed in a horizontal 1% agarose gel in 133 TBE buffer (90 mM Tris-HCl, pH 8.5, 90 mM Boric acid, 2.5 mM EDTA) for 1.5 hours at 100 V as described by Sambrook et al., 1989, "Molecular Cloning: A Laboratory Manual", 2nd Edition, Cold Spring Harbor Lab, New York. The separated PCR DNA products were located in the gel by staining with ethidium bromide and visualizing fluorescent bands with a 365 nm ultraviolet light. Under the PCR conditions described above, a single DNA band (approximately 550 base pairs long) was detected when using this primer combination.

Example 3

Cloning of a 0.55 kb PCR Amplified *S. avermitilis* Genomic DNA Fragment into A. Recovery of the 0.55 kb PCR Product As mentioned before, a 0.55 kb DNA fragment was amplified by PCR using *S. avermitilis* genomic DNA as template and the Rightward plus Leftward primer combination. As shown in FIG. 1 the Rightward primer has an EcoRI recognition site located at the 5' end and the Leftward primer has a XbaI recognition site at the 5' end. The 0.55 kb PCR fragment was cloned using a ligation procedure where both insert and cloning vector were digested with EcoRI and XbaI. Following amplification (as described in Example 2), approximately 80 microliters of the PCR reaction mixture was loaded on a 1% agarose gel and electrophoresed. The 0.55 kb DNA fragment was visualized as described before and recovered by electroelution as follows: The 0.55 kb DNA band was removed using a razor blade and the DNA recovered from the agarose gel by electroelution for 35 min. at 80 V into a V-shaped well filled with 7.5M ammonium acetate using an unidirectional electroelutor (International Biotechnology Inc., New Haven, Conn.). The DNA was then precipitated with ethanol, pelleted and finally redissolved in 20 microliters of DNA buffer (10 mM Tris-HCl, 4 mM NaCl, 0.1 mM EDTA; pH 7.5).

B. EcoRI and XbaI Restriction Enzyme Digestions

The total amount of PCR material recovered above was digested simultaneously with 1 unit each of the restriction enzymes EcoRI and XbaI as recommended by the supplier (Boehringer Mannheim Biochemicals). Similarly, approximately 1 microgram of the plasmid pGEM-3Z (Promega Corp., Madison, Wis.) and 2 units of the restriction enzymes EcoRI and XbaI (all restriction enzymes were purchased from Boehringer Mannheim Biochemicals) were incubated in the assay buffer specified by the supplier, at 37° C. for 4 hours, in a total reaction volume of 60 microliters to produce linear molecules. Then, both the PCR fragment and the linearized vector were each separately extracted twice with an equal volume of phenol-chloroform, twice with an equal volume of ether, and finally the DNAs were precipitated by adding 2 volumes of absolute ethanol. Precipitated DNAs were recovered by centrifugation at 10,000×g for 10 min. and dried under vacuum. The final PCR fragment pellet was redissolved in 20 microliters of DNA buffer, and the final linearized vector pellet was redissolved in 12 microliters of DNA buffer.

C. Ligation to Produce pCD613

About 11 microliters of the EcoRI/XbaI-treated 0.55 kb PCR DNA product, and about 1 microliter of the EcoRI/XbaI-linearized pGEM-3Z were incubated overnight with 1 unit of ligase (New England Biolabs, Inc., Beverly, Mass.) under the conditions specified by the supplier at 15° C. in a total reaction volume of 20 microliters. The reaction was terminated by placing the assay microtube on ice and the reaction mixture (20 microliters) was then used to transform competent *E. coli* DH5-alpha cells following the standard procedure described by Sambrook et al., 1989, "Molecular Cloning: A Laboratory Manual", 2nd Edition, Cold Spring Harbor Lab, New York. Many ampicillin-resistant transformants were recovered. Plasmid vector pGEM-3Z contains a DNA segment derived from the lac operon of *Escherichia coli* that codes for the amino-terminal fragment of beta-galactosidase [Yanisch-Perron, C., Vieira, J., and J. Messing, *Gene*, 33, 103, 1985]. This fragment, whose synthesis can be induced by isopropylthio-beta-D-galactoside (IPTG), is capable of intra-allelic (alpha) complementation with a defective form of beta-galactosidase encoded by the host. *E. coli* cells exposed to the inducer IPTG synthesize both fragments of the enzyme and form blue colonies when plated on media containing the chromogenic substrate 5-bromo-4-chloro-3-indolyl-beta-D-galactoside (X-gal). Insertion of foreign DNA into the polycloning site of the plasmid inactivates the amino-terminal fragment of the beta-galactosidase and abolishes alpha-complementation. Therefore, bacteria carrying recombinant plasmids give rise to white colonies. Numerous white colonies were recovered from this transformation experiment. These colonies should contain the plasmid pCD613. This was confirmed by selecting one colony, designated as strain CD613, and further analyzing. A single bacterial colony of *E. coli* strain CD613 was inoculated into Luria-Bertani (LB) liquid medium containing 50 micrograms/ml of ampicillin following standard microbiological procedures. The LB medium comprised:

| | |
|---|---|
| Bacto-tryptone | 10 g |
| Bacto-yeast extract | 5 g |
| NaCl | 10 g | pH adjusted to 7.0 with 5 N NaOH.
Final volume of the solution adjusted to 1 L.
Sterilized by autoclaving for 20 min at 121° C.

The culture was incubated at 35° C. overnight. The following morning, the bacterial cells were harvested by centrifugation at 10,000 rpm for 5 min. at 4° C. Plasmid vector was isolated from fresh harvested *Escherichia coli* CD613 cells using a modification of the method of Birnboim and Doly (Nucleic Acids Res., 1979, 7:1513–1523), as described by Denoya et al., (*Microbios Lett.*, 1985, 29:87–93). The isolated plasmid DNA was finally dissolved in DNA buffer (10 mM Tris-HCl, 4 mM NaCl, 0.1 mM EDTA; pH 7.5) to produce a concentration of approximately 1 microgram of pCD613 per 10 microliters of buffer. Confirming restriction analysis, using EcoRI and XbaI, showed that, as expected, pCD613 carried the 0.55 kb DNA insert.

Example 4

Preparation of Uniformly Radiolabeled Double-Stranded DNA Probes

Double-stranded DNA probes were prepared by nick translation (see Sambrook et al., 1989, "Molecular Cloning: A Laboratory Manual", 2nd Edition, Cold Spring Harbor Lab, New York), for a general description of this technique). First, a specific DNA fragment carrying the target sequence was prepared by appropriate restriction digestion and purification by electroelution essentially as described in Example 1. Approximately 1 microgram of DNA was labeled in each case using [alpha-$^{32}$P]dCTP (deoxycytidine 5'-triphosphate, tetra(triethylammonium) salt, [alpha-$^{32}$P]-) purchased from NEN-Dupont, and the BRL Nick Translation System purchased from BRL Life Technologies, Inc., following the instructions obtained from the supplier. A typical reaction was performed in a volume of 50 microliters. After addition of 5 microliters of Stop buffer (as described in the BRL recommended procedure), the labeled DNA was separated from unincorporated nucleotides using a Stratagene push column according to the supplier's instructions. $^{32}$P-labeled DNA with a specific activity greatly in excess of $10^8$ cpm/microgram was routinely obtained following these procedures.

Example 5

Analysis of *S. avermitilis* Genomic DNA by Southern Hybridization

Approximately 10 micrograms of purified *S. avermitilis* genomic DNA were digested with 2 units of the restriction enzyme BamHI at 37° C. for a minimum of 2 hours. At the end of the digestion, the DNA fragments were separated by electrophoresis through a 1% agarose gel (see Example 1A), and were transferred overnight to a nylon membrane (pore size 0.45 micrometer) (Schleicher and Schuell Nytran membranes) using the capillary transfer method (Southern, E. M., 1975, *J. Mol. Biol.*, 98:503). The next day, the nylon membranes were wrapped in plastic wrap and the DNA side of each membrane was exposed to a source of ultraviolet irradiation (302 nm) to fix the DNA to the membrane. Hybridization of radiolabeled RNA or DNA probes to DNA immobilized on nylon membranes was performed following the protocol described in Sambrook et al. (1989), "Molecular Cloning: A Laboratory Manual", 2nd Edition, Cold Spring Harbor Lab, New York (hereinafter referred to as "the Sambrook et al. Manual"). Prehybridization and hybridization were carried out at 42° C. Hybridization solution contained: 6×SSC (1×: 0.15M NaCl, 15 mM NaCitrate, pH 7.0), 10×Denhardt's reagent [1×: 0.02% ficoll, 0.02% polyvinylpyrrolidone, 0.02% bovine serum albumin], 1% SDS (sodium dodecyl sulfate), 100 micrograms/ml denatured, fragmented salmon sperm DNA, 100 micrograms/ml *E. coli* tRNA, and 50% formamide (Fluka). After overnight hybridization, membranes were washed as follows: two washes with 1×SSC, 0.1% SDS, at room temperature for 15 minutes, and two washes with 0.1×SSC, 0.1% SDS at 42° C. for 15 minutes. In some experiments hybridization was carried out at 65° C. in the absence of formamide, and SSPE (1×: 0.18M NaCl, 10 mM NaPO$_4$, pH 7.7, 1 mM EDTA) was used instead of SSC. Finally, membranes were exposed to X-ray film to obtain an autoradiographic image.

Example 6

DNA Sequencing

A. Sequencing of Double-Stranded DNA PCR Product Carried in Plasmid pCD613

Supercoiled plasmid pCD613 was prepared as described in Example 2. Approximately 4 micrograms of double-stranded pCD613 were converted to a single-stranded stranded form prior to sequencing. This was accomplished by alkali denaturation as described in the Taq Track Sequencing Systems Technical Manual (Promega Co., Madison, Wis. Oligonucleotide sequencing primers were synthesized by Genosys Biotechnologies, Inc. (Texas). Vector primer 1 (5'-AAGGATCCTGCAGCCCAGTCAC GACGTTGTAAAACGA-3'(SEQ ID NO: 11)) maps upstream of the EcoRI site of the pGEM-3Z multiple cloning site (MCS) (position 2689-2712), and primer 2 (5'-AAGGATCCTCTAGAGGTSSWGTGGKGGCCG ATSCGGWA-3'(SEQ ID NO: 12)) maps downstream of the HindIII site of the MCS (position 91-114).

B. Cloning of the pCD613-derived 0.35 kb SalI *S. avermitilis* genomic fragment into bacteriophage M13 and DNA Sequencing As discussed before, restriction analysis showed that the PCR-derived genomic fragment CD613 contained an internal 0.35 kb SalI fragment. This 0.35 kb SalI *S. avermitilis* DNA fragment was cloned into bacteriophages M13mp18 for the preparation of single-stranded recombinant DNA to be used as templates in Sanger's dideoxy sequencing method (Sanger et al., 1977, Proc. Nat. Acad. Sci. USA, 74:5463–5467). About 2 micrograms of plasmid pCD613, prepared following a miniprep procedure as described before, were digested with the restriction enzyme SalI at 37° C. for 2 hours to release the 0.35 kb *S. avermitilis* genomic fragment. The digestion mixture was electrophoresed in a 1.2% agarose gel, and the 0.35 kb fragment was electroeluted and precipitated as described before. In addition, about 1 microgram of purified double-stranded replicative form (RF) M13mp18 DNA were digested with SalI, dephosphorylated with calf intestine alkaline phosphatase (CIAP) (purchased from Promega Corp., Madison, Wis.), and finally ligated to the 0.35 kb DNA fragment as described previously. Purified RF M13 cloning vector was purchased from New England Biolabs. Ligation mixtures were used to transfect competent *E. coli* JM109 cells. Several white plaques were recovered. Two single white plaques from the mp18 transfection carrying the insert in opposite orientations were selected, phage grown and single-stranded DNA was prepared as described in the Sambrook et al. Manual. DNA sequencing of each single-stranded DNA template was performed using the M13-specific −40 sequencing primer (New England Biolabs, Catalog No. 1212), deoxyadenosine 5'-[alpha-thio]triphosphate, [$^{35}$S] (NEN-Dupont), and the TaqTrack sequencing kit (Promega), following the instructions provided by the supplier (Promega).

C. Transposon-Facilitated Sequencing of Some Genomic Regions Located on the cloned 4.1 kb BamHI Fragment Carrying Part of the bkdF Gene Mini-gamma-delta-1 transposon insertions were used to sequence DNA regions located downstream of the bkdF open reading frame in the cloned 4.1 kb BamHI genomic fragment from *S. avermitilis*. The mini-gamma-delta-1 element is a small (1.8 kb) gamma-delta (Tn1000) derivative that contains the kan gene from Tn5 and the resolution (res) site from gamma-delta cloned between two 40-bp inverted repeats of one of gamma-delta ends (Berg, C. M. et al., 1992, *Gene*, 113:9–16. Mini-gamma-delta-1 lacks the genes encoding transposase and resolvase, and therefore depends on its host to supply transposition and resolution functions. Thus, in strains lacking the helper transposon, mini-gamma-delta-1 will not transpose and the insertion will be stable. Internal to the inverted repeat ends are unique sequences that can be used as primer-binding sites for DNA sequencing. Transposon insertions were prepared essentially as described by Berg C. M. et al., (1993, Methods in Enzymology, Academic Press, vol. 218, p. 279–306). Each inserted transposon was used as the initial template to sequence Streptomyces DNA located at both sites of the insertion. Two "universal" primers were used: "res" primer (5'-GTAGGGAGCCTGATATG-3'(SEQ ID NO: 13)), and "kan" primer (5'-GCTATCCGCGCATCCAT-3'(SEQ ID NO: 14)). Two mini-gamma-delta-1 insertions, named "A3" (clone CD785) and "A5" (clone CD786) were located approximately 1.7 kb and 3 kb from the BamHI end containing the bkdF ORF, respectively. DNA sequencing performed at both ends of each insertion showed that the A3 insertion (sequence CD785) is near the end of the E1-beta ORF (bkdG) (FIG. 5), and the A5 insertion (sequence CD786) is near the end of the E2 ORF (bkdH) (FIG. 6).

Example 7

Cloning of the whole bkd *S. avermitilis* gene cluster and construction of chromosomal map About 4 micrograms of purified pCD61 3 were restricted using SalI restriction enzyme and DNA fragments were separated by electrophoresis in a 1.2% agarose gel. An approximately 0.35 kb SalI DNA fragment, carrying sequence specific for the *S. avermitilis* bkdF E1-alpha gene, was recovered by electroelution, and was labeled by nick translation as described previously. The [$^{32}$P]-labeled DNA fragment was then used as a probe to screen a *S. avermitilis* genomic cosmid library. A detailed description of preparation of genomic libraries in general can be found in the Sambrook et al. Manual. A complete description of streptomycetes chromosomal library preparation is presented in Genetic Manipulation of Streptomyces A Laboratory Manual by Hopwood et al. (1985). A description of cosmid vectors is found in "Cosmid Vectors for Streptomyces Genomic DNA Cloning" by Denoya C. D., U.S. patent application Ser. No. 048,719, filed Apr. 16, 1993.

Ten clones were identified after screening more than 2200 recombinant library clones. The ten hybridizing clones (recorded as *E. coli* clones CD519, CD521, CD691, CD692, CD694, CD695, CD696, CD697, CD698, and CD699) were grown in LB liquid medium and plasmid was prepared from each culture as described before. Restriction end Southern blot hybridization analyses revealed that the ten clones were related, having overlapping chromosomal regions. Interestingly, two of the cosmid clones listed here, namely CD519 and CD521, were also included in the list of cosmid clones identified using a bkdA probe (see C. D. Denoya, U.S. patent application Ser. No. 08/100,518, referred to above). A *S. avermitilis* genomic restriction map, covering the entire chromosomal region including sequence CD613, was obtained following standard procedures, and is presented in FIG. 2. This Figure also shows the linkage between the novel bkd genes described here, and those described previously (C. D. Denoya, U.S. patent application Ser. No. 08/100,518, filed Jul. 30, 1993). Both bkd gene clusters are located approximately 12 kb apart.

Example 8

Transformation of *Streptomyces lividans* with Shuttle Vectors and Large Scale Preparation of Plasmid Vectors from *S. lividans* Transformants

*S. lividans* strain TK64 was used in these experiments. The media for growing and protoplasting *S. lividans*, and the preparation of protoplasts and transformation were performed as described by D. A. Hopwood et al., Genetic Manipulation of Streptomyces—a laboratory manual, 1985, The John Innes Foundation, Norwich, U.K. In addition, the latter reference provides a full description of *S. lividans* strain TK64. *S. lividans* protoplasts transformed directly with shuttle vector pCD262, or with a number of derivatives, were selected for thiostrepton resistance. Plasmid DNAs were prepared from selected transformants as follows: Cultures were grown in liquid YEME medium (Bibb, M. J., Freeman, R. F., and D. A. Hopwood, 1977, *Mol. Gen. Genetics*, 154:155–166). YEME medium contained per liter: 3 g yeast extract, 5 g bacto-peptone, 3 g malt extract, 340 g sucrose. After autoclaving, 2 ml of 2.5M $MgCl_2.6H_2O$ were added. Cultures were grown for 40–48 hours at 30° C. Mycelium from 500 ml culture of streptomycetes cells were harvested by centrifugation, and resuspended to a final volume of 50 ml with lysozyme solution (2 mg/ml lysozyme in 0.3M sucrose, 0.025M Tris-HCl (pH 8.0), and 0.025M EDTA). After this step, plasmids were prepared following an alkaline lysis procedure, essentially as described in the manual: "Genetic Manipulation of Streptomyces, A Laboratory Manual", The John Innes Foundation, Norwich, 1985. DNA pellets were redissolved in 500 ml 10 mM Tris-HCl, pH 8.0, 1 mM EDTA, and further purified by caesium chloride-ethidium bromide gradient ultracentrifugation essentially as described in the Sambrook et al. Manual. The isolated plasmid DNA is finally dissolved in DNA buffer (10 mM Tris-HCl, 4 mM NaCl, 0.1 mM EDTA; pH 7.5) to produce a concentration of approximately 1 microgram of plasmid DNA per 10 microliters of buffer.

Example 9

Construction of a *S. avermitilis* bkdF mutant

The technique used for introducing the chromosomal deletion is a variation of the gene replacement methods used in *Saccharomyces cerevisiae, Escherichia coli*, and *Bacillus subtilis* (Scherer, S. and R. W. Davis, 1979, *Proc. Natl. Acad. Sci. U.S.A.*, 76:4951–4955; Shortle, D. et al., 1982, *Science*, 217:371–373; Stahl, M. L., and Ferrari, E., 1984, *J. Bacteriol.*, 158:411–418). A general description of this technology, specifically applied to Streptomyces, can be found in the review paper "Genetic Manipulation of Streptomyces: Integrating Vectors and Gene Replacement", by Kieser, T., and Hopwood, D. A., 1991, in: Methods in Enzymology, vol. 204, 430–458. Furthermore, a detailed description of this technique, including an additional protoplasting step, necessary to assure single colony isolates and to increase the frequency of plasmid elimination, can be found in the paper authored by Anzai et al., entitled "Replacement of *Streptomyces hygroscopicus* genomic segments with in vitro altered DNA sequences", published in The Journal of Antibiotics, 1988, vol. XLI, No. 2, pp. 226–233. The protoplasting and regeneration step often stimulates plasmid loss. However, most of the bifunctional (*E. coli*/Streptomyces) vectors (such as pCD262, used in this work) give rise to occasional plasmid-free cells after one or two rounds of nonselective growth (Kieser, T., and Hopwood, D. A., 1991, in: *Methods in Enzymology*, vol. 204, 430–458).

A. Construction of Shuttle Vector Carrying Inactivated Copy of the bkdF Gene

As shown in FIG. 7, three adjacent BamHI restriction fragments in the *S. avermitilis* chromosome region comprising the bkd gene cluster discussed here were mapped (from left to right): 2.3 kb, 1.4 kb and 4.1 kb. The 1.4 kb BamHI genomic fragment carries the beginning of the E1-alpha open reading frame (ORF-1) (bkdF). The 4.1 kb BamHI carries the rest of the bkd gene cluster (end of bkdF, bkdG, and bkdH). Each of these three restriction fragments were subcloned into *E. coli* vector pGEM-3Z. The resulting constructs were: Plasmid pCD740, carrying the 2.3 kb BamHI fragment; plasmid pCD854, carrying the 1.4 kb BamHI fragment; and plasmid pCD713, carrying the 4.1 kb BamHI fragment (see FIG. 2). The construction of the vector carrying the inactivated copy of the bkdF gene was carried out in two steps. First, both the 4.1 kb BamHI *S. avermitilis* fragment and the 1.6 kb BglII fragment carrying the ermE marker, which confers resistance to the antibiotic erythromycin, were cloned into shuttle vector pCD262 (C. D. Denoya, "Novel Bacterial Plasmid Shuttle Vectors for Streptomyces sp. and *Escherichia coli*", U.S. patent application Ser. No. 032,925, filed Mar. 18, 1993) as follows: Approximately 1.5 micrograms of plasmid pCD713 was cut with the restriction enzyme BamHI and electrophoresed on a 0.8% agarose gel. After electrophoresis, the 4.1 kb BamHI fragment was recovered from the gel using the GeneCleanII kit and the procedures recommended by the manufacturer (Bio 101 Inc., La Jolla, Calif.). Similarly, approximately 2 micrograms of pIJ4026 was cut with the restriction enzyme BglII and electrophoresed on a 0.8% agarose gel. Plasmid pIJ4026 is a derivative of the *E. coli* cloning vector pUC18 carrying the ermE gene of *Saccharopolyspora erythraea* (formerly *Streptomyces erythraeus*) (see M. Bibb et al., 1985, *Gene*, 41:357–368, and D. A. Hopwood et al., Genetic Manipulation of Streptomyces—A Laboratory manual, 1985, The John Innes Foundation, Norwich, U.K.). After electrophoresis, the 1.6 kb BglII fragment was recovered from the gel using the GeneCleanII kit and the procedures recommended by the manufacturer (Bio 101 Inc., La Jolla, Calif.). In addition, an aliquot of purified plasmid pCD262 was linearized with the restriction enzyme BglII, dephosphorylated with calf intestine alkaline phosphatase (CIAP) (purchased from Promega Corp., Madison, Wis.), and finally ligated to the 4.1 kb BamHI, and the 1.6 kb BglII purified fragments described above. The ligation reaction was terminated by placing the assay microtube on ice and the reaction mixture (20 microliters) was then used to transform competent *E. coli* DH5-alpha cells following standard procedure as described in Example 1. Many ampicillin-resistant transformants were recovered. These colonies should contain the plasmid pCD761. This was confirmed by selecting one colony, designated as strain CD761, and further analyzing the recombinant plasmid recovered from this strain with several restriction enzymes. Plasmid pCD761 is a derivative of the shuttle vector pCD262, carrying both the 4.1 kb *S. avermitilis* BamHI genomic fragment, and the 1.6 kb BglII DNA fragment carrying the ermE marker, both oriented as shown in FIG. 7. Secondly, plasmid pCD761 was linearized with BglII, dephosphorylated using CIAP, and ligated to the 2.3 kb BamHI *S. avermitilis* fragment isolated from plasmid pCD740. The ligation reaction was terminated by placing the assay microtube on ice and the reaction mixture (20 microliters) was then used to transform competent *E. coli* DH5-alpha cells following standard procedure as described in Example 1. Many ampicillin-resistant transformants were recovered. These colonies should contain the plasmid pCD768. This was confirmed by selecting one colony, designated as strain CD768, and further analyzing the recombinant plasmid recovered from this strain with several restriction enzymes. Plasmid pCD768 is a derivative of shuttle vector pCD262 carrying two *S. avermitilis* genomic fragments (2.3 and 4.1 kb BamHI) which are adjacent on each side of the 1.4 kb BamHI fragment on the wild type chromosome. In addition, pCD768 carries the ermE marker located between the 2.3 and the 4.1 kb BamHI fragments. The ermE marker lies in the opposite orientation to that of the ORF-1 (bkdF), to avoid possible difficulties caused by overexpression of downstream genes. This construct produces a 1.4 kb deletion, affecting the 5' end of the bkdF gene, in the host genome upon recombination.

B. Transformation of *Streptomyces avermitilis* with Shuttle Vectors

Shuttle vectors (pCD262, pCD768) used to transform *S. avermitilis* protoplasts were prepared either from transformed *E. coli* DH5-alpha or *E. coli* CD167 cells (strain CD167 is a single colony isolate derived from *E. coli* GM2163—which was obtained from Dr. B. J. Bachmann, Curator, *E. coli* Genetic Stock Center, Yale University) (see Example 1) or from transformed *S. lividans* TK64 cells (see Example 8).

*S. avermitilis* strain ATCC 31272 single colony isolate #2 (SC2) was used throughout. Three alternative inocula were used to prepare *S. avermitilis* protoplasts: 1. Spores (prepared as described by Hopwood et al., 1985, Genetic Manipulation of Streptomyces—A Laboratory Manual, The John Innes Foundation, Norwich, U.K.), 2. Frozen Sonicated Mycelia (see preparation below), and 3. Colonies on YPD-2 agar (see Example 1). Frozen sonicated mycelia were prepared as follows: Mycelial cultures were grown in Trypticase Soy Broth (TSB) to a turbidity of 2 to 9 at 600 nm and then homogenized 10 times with a glass tissue grinder. The homogenized mycelia were diluted two-fold in TSB and 20 ml was added to a sterile polypropylene centrifuge tube. An ultrasonic probe (Bronwill Biosonik III) was submerged to a depth of 1 to 2 cm into the liquid, and the sample sonicated at 50% intensity (half maximum wattage) for 10 sec. Sonication dispersed the mycelial masses into single or double cellular units which produced rapid exponential growth when subcultured. Sonicated mycelial preparations were diluted to a final concentration of 40% glycerol, pipetted into vials, and frozen at −85° C. Spores, mycelia, or homogenized colonies were inoculated into YEME medium (see Example 1) containing 0.5% glycine. Preparation of *S. avermitilis* protoplasts and transformation protocol were performed as described by D. A. Hopwood et al, Genetic Manipulation of Streptomyces—A Laboratory Manual, 1985, The John Innes Foundation, Norwich, U.K., following modifications as described by MacNeil, D. J., and Klapko, L. M., *J. Industrial Microbiol.*, 1987, 2, 209–218. *S. avermitilis* protoplasts transformed with shuttle vector pCD262, or a derivative such as pCD768, were selected for thiostrepton or erythromycin resistance, respectively.

C. Isolation of *S. avermitilis* Erythromycin-Resistant, Thiostrepton-Sensitive Mutant using pCD768

Plasmid pCD768 was transformed into protoplasts of *S. avermitilis* 31272 SC2 as described above. Primary transformants of *S. avermitilis* were selected with 4 micrograms of erythromycin per ml on regeneration medium (RM14) plates (see above for reference describing the media composition). Two erythromycin-resistant (erm-R) transformants (Nos. 1 & 2) were picked onto YPD-2 agar plates (see Example 1) containing either 4 micrograms/ml of erythromycin or 4 micrograms/ml of thiostrepton. Both transformants were resistant to both antibiotics (erm-R, tsr-R). Transformant #1 (named *S. avermitilis* strain CD783) was selected for further work. This strain was grown in YEME liquid medium and protoplasts were prepared and plated on regeneration medium plates containing erythromycin (4 micrograms/ml). This protoplast regeneration step was included to assure single colony isolation and also to increase plasmid loss (Anzai, H., et al., 1988, "Replacement of *Streptomyces hygroscopicus* genomic segments with in vitro altered DNA sequences", *The Journal of Antibiotics*, voL XLI, No. 2, pp. 226–233). Numerous colonies were regenerated and fifty clones were picked onto plates containing erythromycin or thiostrepton. Forty-six out of fifty colonies were able to grow on thiostrepton. Summarizing, 46 colonies were erm-R, tsr-R, and only 4 colonies were erm-R, tsr-S. The erm-R, tsr-S colonies presented the phenotype expected after the integration had formed (double crossover events) and the free replicon had been lost. Therefore, the 4 clones that presented the erm-R and tsr-S phenotype (pp15, pp17, pp22, and pp40), together with 2 clones that were erm-R, tsr-R (used as control) (pp14, and pp21), were further analyzed.

D. *S. avermitilis* bkdF Mutant: Phenotype of *S. avermitilis* Carrying a Chromosomal Deletion Affecting the 5' End of the bkdF Gene The following analysis were performed: 1. Ability to grow on minimal media agar plates containing isoleucine, leucine, and valine (ILV) as sole carbon (C) sources; 2. Assay of Branched Chain Alpha-Ketoacid Dehydrogenase (BCKDH) E1 activity; and 3. Ability to produce natural and novel avermectins during fermentation. A description of these methods follows:

1. ILV Plates: A variation of the classical M9 minimal medium (Anderson, E. H., 1946, *Proc. Natl. Acad. Sci. U.S.A.*, 32:120–128) was used. The modified M9 medium comprised (per liter):

| Agarose (Seakem ME, FMC BioProducts, Rockland, ME) | 7.5 g |
|---|---|
| Distilled H2O | 650 ml |

Autoclaved for 15 minutes at 121° C. When cooled, the following sterile solutions were added:

| 25 × M9 Salts solution | 40 ml |
|---|---|
| Mineral stock solution | 2.1 ml |
| 0.1 M FeSO$_4$.7H$_2$O | 0.1 ml |
| ILV mix | 250 ml |
| pH adjusted to 7.0 | |
| Final volume: 1 liter. | |
| Approximately 25 ml were poured per plate. | |

25×M9 salts was made by dissolving the following salts in deionized H$_2$O to a final volume of 1.2 L:

| K$_2$HPO$_4$ | 125 g |
|---|---|
| NaH$_2$PO$_4$.H$_2$O | 55 g |
| NaNO$_3$ | 48 g |
| pH adjusted to 7.0 | |

The salt solution was divided into 160-ml aliquots and sterilized by autoclaving for 15 minutes at 121° C.
Mineral stock solution comprised:
1M MgSO$_4$.7H$_2$O
1M CaCl$_2$
0.25M MnSO$_4$.H$_2$O
Autoclaved for 15 minutes at 121° C.

ILV mix was prepared by dissolving 10 g each of L-isoleucine, L-leucine, and L-valine in 1 L deionized H$_2$O. Mix was sterilized by filtration.

On these plates bkd-deficient mutants were unable to grow. ILV nonutilizers were scored after 14 days incubation at 29° C.

2. BCKDH E1 Assay: BCKDH E1 activity was determined by a modified version of the radiochemical assay described previously (Hafner, E. W. et al., 1991, *J. Antibiotics*, 44:349–356). Selected isolates were grown on YPD-2 agar plates for 6–7 days at 29° C. After growth, a "pinhead" sized clump of cells was picked up from each colony growing on the YPD-2 agar plates using a sterile toothpick and transferred to the bottom of a 15-ml glass scintillation vial. The cells were resuspended and permeabilized by the addition of 100 microliters of the toluene/alpha-[1-$^{14}$C] ketoisocaproate mix (prepared as described later). The mouth of the vial was immediately covered with Whatman 4CHR paper (Whatman catalog number 3004614) that has been impregnated with Solvable (a tissue and gel solubilizer purchased from NEN-Dupont). A plastic cap was then firmly placed on the vial, both the cap and the upper half of the vial were wrapped with parafilm, and incubated with gentle shaking for 3.5 hours at 29° C. At the completion of the incubation, the filter paper was transferred to a 7-ml glass scintillation vial containing 4 ml "Ready Safe" (Beckman) liquid scintillation cocktail to determine radioactivity. Radioactivity was measured after equilibration-in this solvent for 4 hours or more. The toluene/alpha-[1-$^{14}$C] ketoisocaproate mix was prepared by adding 22 microliters of the alpha-[1-$^{14}$C] ketoisocaproate stock solution to 1 ml M9 salts medium (Davis, R. W., et al., 1980, Appendix 1: Media, drug concentrations, and nutritional supplements In "A Manual for Genetic Engineering—Advanced Bacterial Genetics", p. 203, Cold Spring Harbor Laboratory, New York) containing 5% toluene which had been sonicated to produce a milky-white dispersion of the toluene. The alpha-[1-$^{14}$C] ketoisocaproate stock solution was prepared by mixing 2.8 microliters of 20 mM alpha-ketoisocaproate (sodium salt, Sigma K-0629), 50 microliters of alpha-[1-$^{14}$C] ketoisocaproate (55 mCi/mmol, 50 microCuries/ml, Amersham), and enough H$_2$O to a final volume of 1 ml.

Protein concentration was determined by using the Bio-Rad protein assay (Bio-Rad Laboratories, Richmond, Calif.), which is based on the Bradford dye-binding procedure (Bradford, M., *Anal. Biochem.*, 72:248, 1976). The specific activity of the E1 component of the branched-chain alpha-ketoacid dehydrogenase is expressed as picomoles of $CO_2$ evolved per minute per milligram of protein (Table I).

3. Avermectin Production: Either *S. avermitilis* ATCC 31272 SC2 or *S. avermitilis* strain CD794 (bkdF) mycelium grown on a fresh, modified YPD-2 agar plates (the modification consisted of the omission of acetate from the regular YPD-2 medium, see Example 1) for five to seven days was inoculated into a 50-ml (1×6 inch) culture tube containing 8 ml of minimal defined medium (see below). The tube was then shaken at a 45° angle at 200 RPM at 29° C. for 72 hours. After growth, a 2-ml aliquot of the seed culture was used to inoculate a new 300-ml flask containing 25 ml of minimal defined medium to which various additions of fatty acids could be made. The fermentation medium was made up as described previously (Hafner, E. W. et al., 1991, *J. Antibiotics*, 44:349–356) except that hydrolyzed starch (114 g/liter) was used instead of thinned and potato soluble starch, leucine and NaCl were omitted, and glycine (2 g/liter) was added. In some fermentations, either S(+)-2-methylbutyric acid or cyclohexane carboxylic acid (CHC) were added to the medium (0.04% final concentration). After 12 days of shaking (200 RPM) at 29° C., the flask contents were extracted with 4 volumes of an acetonitrile-methanol (7:118) solvent mixture and the supernatant was analyzed for avermectins by high performance liquid chromatography (HPLC). The HPLC assay was carried out using a Beckman 5 micrometers Ultrasphere ODS C-18 column (4.6 mm×25 cm), with a flow of 0.75 ml/minute and detection by absorbance measurements at 240 nm. The mobile phase was water (178 ml), acetonitrile (102 ml), and methanol to a final volume of 2 liters.

Table I below summarizes these results. The four thiostrepton-sensitive clones, which have lost the free replicon, exhibited a typical bkd-deficient phenotype, as follows: All 4 clones were unable to grow on ILV minimal medium plates and had no activity when assayed for the E1 component of the BCKDH complex. Fermentation studies showed that the blocked cultures were unable to synthesize natural avermectins. In addition, when S(+)-2-methylbutyric acid was added to the fermentation medium (0.04%) final concentration), natural "a" forms of avermectin were synthesized; similarly, addition of cyclohexane carboxylic acid (CHC) led to the formation of novel CHC-avermectins. These fermentation results demonstrated that the bkd block did not affect the avermectin biosynthetic cellular machinery. One clone out of this group of 4 (clone pp15, see Table I) was formally named *S. avermitilis* strain CD794 and is being deposited in the American Type Culture Collection as an example of this invention.

TABLE I

E1 BRANCHED-CHAIN ALPHA-KETOACID DEHYDROGENASE ACTIVITY IN VARIOUS *S. AVERMITILIS* STRAINS

| *S. avermitilis* strain[a] | Resistance phenotype[b] | Growth on ILV[c] | E1 BCKDH specific activity[d,e] | Production of natural avermectins[f] |
|---|---|---|---|---|
| ATCC 31272 SC2 | Erm-S, Tsr-S | + | 69 | + |
| PF 402-77 | Erm-S, Tsr-S | − | 0[g] | −/+[i] |
| CD783 | Erm-R, Tsr-R | + | 67 | + |
| pp14 | Erm-R, Tsr-R | + | 65 | + |
| pp21 | Erm-R, Tsr-R | + | 50 | + |
| pp15 (CD794) | Erm-R, Tsr-S | − | 0[g] | −/+[i] |
| pp17 | Erm-R, Tsr-S | − | 0[g] | NT[h] |
| pp22 | Erm-R, Tsr-S | − | 0[g] | −/+[i] |
| pp40 | Erm-R, Tsr-S | − | 0[g] | NT[h] |

[a]The following *S. avermitilis* were used: ATCC 31272 SC2, a single colony isolate of strain ATCC 31272; PF402-77, a bkd-deficient mutant derivative of strain ATCC 31272 SC2 and produced by chemical mutagenesis; CD783, a derivative of strain ATCC 31272 SC2 transformed with plasmid pCD768 (see Example 9); pp14–40, single colony derivatives of CD783 isolated after protoplasting and regeneration (see Example 9).
[b]Erm-R, resistant to erythromycin; Tsr-R, resistant to thiostrepton.
[c]+ or −, ability or inability to grow on minimal medium supplemented with Isoleucine, Leucine, and Valine, as sole carbon sources.
[d]The specific activity of the E1 component of the branched-chain alpha ketoacid dehydrogenase as picomoles of $CO_2$ evolved per minute per milligram of protein.
[e]The results are the means of duplicate determinations.
[f]+ or −, production of non-production of natural avermectins by fermentation.
[g]0 = not dectable.
[h]NT, not tested.
[i]−/+ = non-production of natural avermectins by fermentation; however, production of natural avermectin when S(+)-2-methylbutyric acid was added to the fermentation medium and production of novel CHC-avermectins when CHC was added to the fermentation medium.

E. Southern Hybridization Analyses to Confirm the bkd-minus Genotype

Southern hybridization analyses were performed on two of the erm-R, tsr-S clones, pp15 (formally named strain CD794) and pp22 (formally named strain CD798). These analyses showed that chromosomal integration of the ermE marker, and concomitant deletion of the 1.4 kb BamHI genomic fragment that carries the 5′ end of the bkdF open reading frame (ORF-1) had occurred by a double crossover. Restriction fragments of chromosomal DNA were resolved by electrophoresis through a 1% agarose gel and transferred to nylon essentially by the method of Southern (1975) as described in Example 5.

Example 10

Construction of a *S. avermitilis* bkdABCF Mutant

This example describes the construction of a stable *S. avermitilis* multiple mutant affecting the following bkd genes: bkdA, bkdB, bkdC, and bkdF. The first three of these genes—bkdA, bkdB, bkdC, encode the E1-alpha, E1-beta and E2 subunits of the branched chain alpha-ketoacid dehydrogenase complex, respectively. These genes are part of the bkdABC gene cluster, as described by Denoya, C. D., U.S. patent application Ser. No. 08/100,518, filed Jul. 30, 1993. The bkdF gene is located in the bkdFGH gene cluster described above, and encodes the E1-alpha subunit of the branched chain alpha-ketoacid dehydrogenase complex.

A. Design and Construction of Delivery Vector Carrying Target Chromosomal Region (bkdC) Marked with a Selectable, Antibiotic-resistance Marker (ermE)

Figure 9:
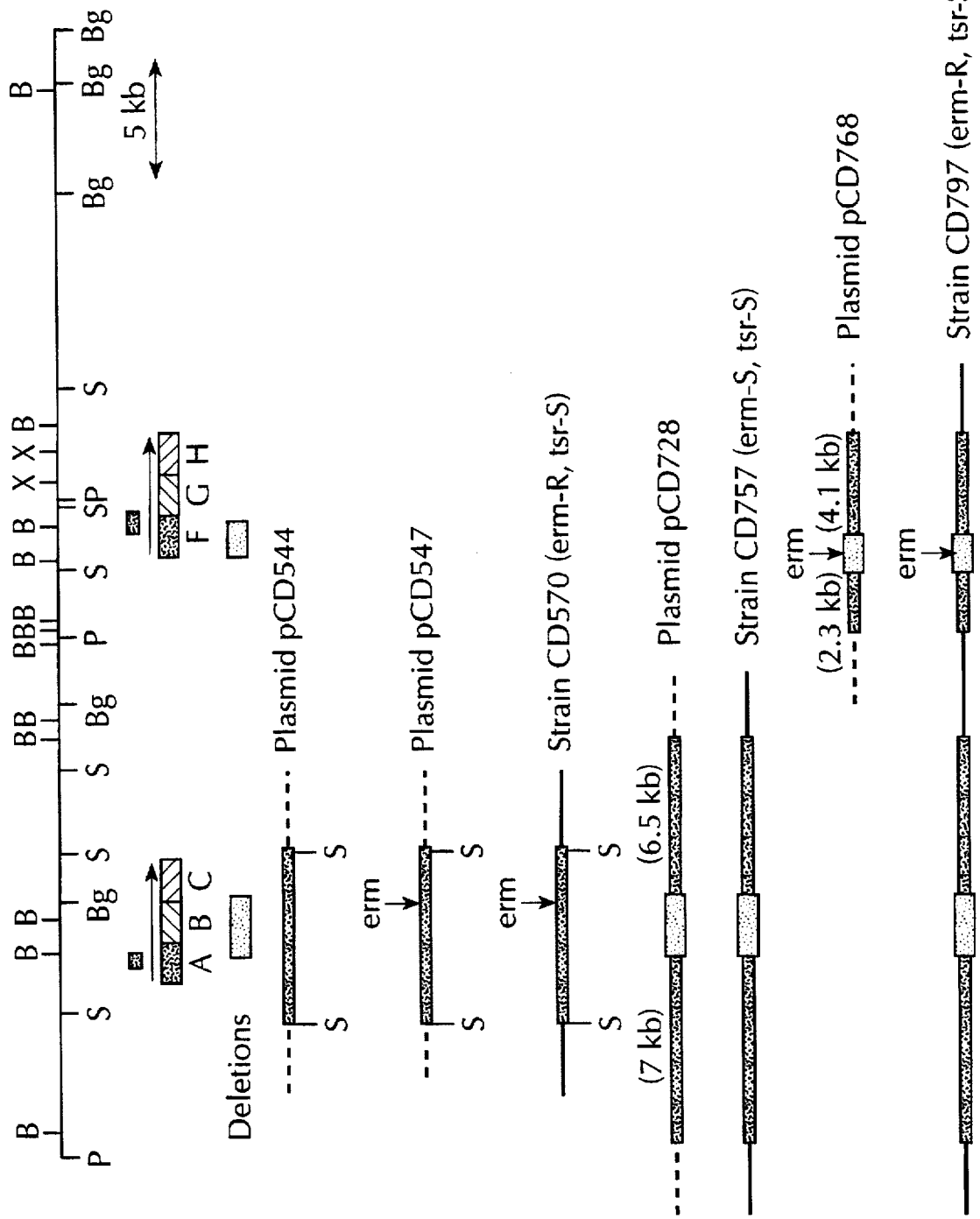
FIG. 9: Construction of the bkdABCF mutant. Genomic restriction map and simplified drawings of vector constructs and target genomic regions are represented. Location of bkd gene clusters, orientation of open reading frames, and abbreviations were used as described in the legend for FIG. 3. Deleted segments are indicated as a gray shaded area. Continuous and dashed lines represent chromosomal and vector DNA, respectively. Thick black lines represent cloned genomic fragments used in gene replacement. Vertical arrows indicate the location of antibiotic resistance marker insertion.

First, the 6.5 kb SphI S. avermitilis 31272 genomic fragment (carrying the bkdABC gene cluster) was subcloned into the SphI cloning site of shuttle/delivery vector pCD500 (see Denoya, C. D., "Novel Bacterial Plasmid Shuttle Vectors for Streptomycetes and Escherichia coli", U.S. patent application Ser. No. 08/032,925, filed Mar. 18, 1993), resulting in plasmid pCD544 (see FIG. 9). Subsequently, the 1.7 kb BglII plJ4026 fragment carrying the ermE marker was inserted into the unique BglII site present in the pCD544 insert. Plasmid plJ4026 is a derivative of the E. coli cloning vector pUC18 carrying the ermE gene of Saccharopolyspora erythraea (formerly Streptomyces erythraeus) (see M. Bibb et al., 1985, Gene, 41:357–368, and D. A. Hopwood et al., Genetic Manipulation of Streptomyces—A Laboratory Manual, 1985, The John Innes Foundation, Norwich, U.K.). The resulting construction (pCD547) has an insertionally inactivated copy of the bkdC gene.

B. Construction of a Genetically Marked bkdC Mutant Strain

Using plasmid pCD547 as the delivery vector (see previous section), S. avermitilis wild type strain ATCC 31272 SC2 as the host, and following standard gene replacement procedures (see Example 9), twelve protoplasted/then regenerated single colonies showing an erythromycin-resistant thiostrepton-sensitive phenotype were selected. One colony out of this group of 12 was formally named S. avermitilis strain CD570 (see FIG. 9), and it was used as a host in the following gene replacement steps (see below).

C. Design and Construction of Delivery Vector Carrying Mutated (deleted) bkdABC Target Region Plasmid pCD728 is a derivative of shuttle vector pCD262 (see Denoya, C. D., "Novel Bacterial Plasmid Shuttle Vectors for Streptomycetes and Escherichia coli", U.S. patent application Ser. No. 08/032,925, filed Mar. 18, 1993) carrying two S. avermitilis chromosomal fragments (7 kb BamHI, prepared from subclone pCD528, and 6.5 kb BglII/BamHI, prepared from subclone pCD559 (see FIG. 9). For a full description of the subclones utilized here see also Denoya, C. D., U.S. patent application Ser. No. 08/100,518, filed Jul. 30, 1993.

D. Construction of Unmarked, bkdABC Deleted Strain

Plasmid pCD728 was transformed into protoplasts of S. avermitilis strain CD570 and putative transformants were recovered. A control plasmid, pCD739, with one of the genomic fragments inserted in the wrong orientation, was also introduced in strain CD570 by transformation. Many recombinants were obtained in which the ermE marker had been replaced by the bkdABC deleted construct and the delivery plasmid (pCD262) had been lost from the cells. Summarizing, upon transformation and double crossover recombination, pCD728 produced a deletion of about 2 kb of the S. avermitilis chromosome affecting bkdA (E1-alpha), bkdB (E1-beta), and bkdC (E2) genes. The recovered integrants had an erythromycin-sensitive, thiostrepton-sensitive phenotype. Southern blot analysis confirmed that the ermE marker was replaced by the deleted sequence. One single colony, representative of this group, was selected for further work and recorded as strain CD757 (see FIG. 9).

E. Design and Construction of the bkdF Gene Replacement Vector

The construction of this vector was described in Example 9, section A. Briefly, plasmid pCD768 is a derivative of shuttle vector pCD262 carrying two S. avermitilis genomic fragments (2.3 and 4.1 kb BamHI) which are adjacent on each side of the 1.4 kb BamHI fragment on the wild type chromosome. In addition, pCD768 carriers the ermE marker located between the 2.3 and the 4.1 kb BamHI fragments. The ermE marker lies in the opposite orientation to that of the ORF-1 (bkdF), to avoid a possible lethality caused by overexpression of downstream genes. This construct produced a 1.4 kb deletion (affecting the 5' end of the bkdF gene) in the host genome upon recombination.

F. Construction of a S. avermitilis Multiple bkd Mutant (bkdABCF)

Plasmid pCD768 was transformed into protoplasts of S. avermitilis strain CD757 (bkdABC) (see step D, above) essentially as described in Example 9. Many transformants were recovered and putative integrants were selected following the standard protocol. One integrant, representative of this group and showing an erythromycin-resistant, thiostrepton-sensitive phenotype was named strain CD797 and further analyzed (see FIG. 9). Culture CD797 exhibited a typical bkd-deficient phenotype, as follows: it was unable to grow on ILV minimal medium plates (see Example 9, and had no activity when assayed for the E1 component of the BCKDH complex. Fermentation studies showed that the blocked culture was unable to synthesize natural avermectins unless supplemented with either S(+)-2 methylbutyric acid or isobutyric acid. Also, addition of cyclohexane carboxylic acid (CHC) led to the formation of novel CHC-avermectins. These fermentation results demonstrated that the multiple bkd block, comprising disruption or deletion of four bkd genes (bkdA, bkdB, bkdC, and bkdF), did not affect the avermectin biosynthetic cellular machinery.

---

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 501 base pairs
( B ) TYPE: nucleic acid ( C ) STRANDEDNESS: double
( D ) TOPOLOGY: linear ( i i ) MOLECULE TYPE: cDNA ( x i ) SEQUENCE DESCRIPTION: SEQ ID NO:1:

| | | | | | |
|---|---|---|---|---|---|
| TACGTCTTCC | CGACCTACCG | CGAGCACGGC | GTCGCCTGGT | CCGGCGGGGT | CGACCCCACC | 60
| AACCTGCTCG | GCATGTTCCG | CGGCGTGAAC | AACGGCGGCT | GGGATCCCAA | CAGCAACAAC | 120
| TTCCACCTCT | ACACGATCGT | CATCGGCTCG | CAGACGCTGC | ACGCCACCGG | CTACGCCATG | 180
| GGTATCGCCA | AGGACGGCGC | CGACTCGGCC | GTGATCGCGT | ACTTCGGTGA | CGGCGCCTCC | 240
| AGCCAGGGTG | ACGTCGCCGA | ATCGTTCGCC | TTCTCCGCGG | TCTACAACGC | CCCTGTCGTC | 300
| TTCTTCTGCC | AGAACAACCA | GTGGGCGATC | TCGAGCCCCA | CCGAGAAGCA | GACCCGCGTC | 360
| CCGCTCTACC | AGCGCGCGCA | GGGCTACGGC | TTCCCGGGCG | TCCGCGTCGA | CGGCAACGAC | 420
| GTACTGGCCT | GCCTCGCCGT | CACCAAGTGC | CTCGAGCGGG | CCCGCCGGGG | CGAGGGGCCC | 480
| ACGTTGGTCG | AGGCGTTCAC | G | | | | 501

( 2 ) INFORMATION FOR SEQ ID NO:2:

( i ) SEQUENCE CHARACTERISTICS:
( A ) LENGTH: 201 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:2:

| | | | | | |
|---|---|---|---|---|---|
| CTCGCCGAGT | CGGGCATCGT | CGGCACGGCG | ATCGGTCTCG | CCCTGCGCGG | CTACCGGCCG | 60
| GTGGTGGAGA | TCCAGTTCGA | CGGCTTCGTC | TTCCCGGCGT | ACGACCAGAT | CGTCACGCAG | 120
| CTCGCGAAGA | TGCACGCGCG | GGCGTCGGGC | AAGATCAAGC | TCCCCGTTGT | CGTCCGCATC | 180
| CCGTACGGCG | GCGGCATCGG | C | | | | 201

( 2 ) INFORMATION FOR SEQ ID NO:3:

( i ) SEQUENCE CHARACTERISTICS:
( A ) LENGTH: 217 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| CGCCGGTGTT | CCTGGGCGGC | GGGCCGCCGG | AGATCGCCGC | CCGCATCACG | GAGCGCTGCT | 60
| TCTACCACCT | GGAGGCACCC | GTGCTGAGGG | TCGGCGGCTA | CCACGCCCCG | TATCCGCCGG | 120
| CGCGTCTGGA | AGAGGAGTAC | CTTCCGGGCC | TTGACCGGGT | GCTCGATGCC | GTCGACCGCT | 180
| CGCTGGCGTA | CTGAGGAGAG | GGTCGTGACG | ACGATGA | | | 217

( 2 ) INFORMATION FOR SEQ ID NO:4:

( i ) SEQUENCE CHARACTERISTICS:
( A ) LENGTH: 453 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:4:

-continued

```
AACCAGGAGA  TCGTCCTCAA  GCACTATGTG  AACCTGGGCA  TCGCGGCGGC  CACCCCGCGC    60

GGTCTGATCG  TCCCGAACAT  CAAGGACGCC  CACGCCAAGA  CCGTGCCGCA  ACTGGCCGAG   120

TCACTGGGTG  AGTTGGTGTC  GACGGCCCGC  GAGGGCAAGA  CGTCCCCGAC  GGCCATGCAG   180

GGCGGCACGG  TCACGATCAC  GAACGTCGGC  GTTCTTCGGC  GTCGACACGG  GCACGCCGAT   240

CCTATCCTCA  ACCCCGGCGA  GTCCGCGATC  CTCGGCTTCG  GCGCGATCAA  GCTCCAGCCG   300

TGGGTCCACA  AGGGCAAGGT  CAAGCCCCGA  CAGGTCACCA  CGCTGGCGCT  CAGCTTCGAC   360

CATCGCCTGG  TCGACGGCGA  GCTGGGCTCC  AAGGTGCTGG  CCGACGTGGC  GGCGATCCTG   420

GAGCAGCCGA  AGCGGCTGAT  CACCTGGGCC  TAG                                 453
```

( 2 ) INFORMATION FOR SEQ ID NO:5:

( i ) SEQUENCE CHARACTERISTICS:
        ( A ) LENGTH: 167 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Tyr  Val  Phe  Pro  Thr  Tyr  Arg  Glu  His  Gly  Val  Ala  Trp  Ser  Gly  Gly
 1              5                        10                       15

Val  Asp  Pro  Thr  Asn  Leu  Leu  Gly  Met  Phe  Arg  Gly  Val  Asn  Asn  Gly
               20                        25                       30

Gly  Trp  Asp  Pro  Asn  Ser  Asn  Asn  Phe  His  Leu  Tyr  Thr  Ile  Val  Ile
                    35                   40                  45

Gly  Ser  Gln  Thr  Leu  His  Ala  Thr  Gly  Tyr  Ala  Met  Gly  Ile  Ala  Lys
          50                        55                  60

Asp  Gly  Ala  Asp  Ser  Ala  Val  Ile  Ala  Tyr  Phe  Gly  Asp  Gly  Ala  Ser
65                        70                       75                       80

Ser  Gln  Gly  Asp  Val  Ala  Glu  Ser  Phe  Ala  Phe  Ser  Ala  Val  Tyr  Asn
                    85                       90                       95

Ala  Pro  Val  Val  Phe  Phe  Cys  Gln  Asn  Asn  Gln  Trp  Ala  Ile  Ser  Ser
               100                      105                     110

Pro  Thr  Glu  Lys  Gln  Thr  Arg  Val  Pro  Leu  Tyr  Gln  Arg  Ala  Gln  Gly
          115                           120                     125

Tyr  Gly  Phe  Pro  Gly  Val  Arg  Val  Asp  Gly  Asn  Asp  Val  Leu  Ala  Cys
     130                      135                      140

Leu  Ala  Val  Thr  Lys  Cys  Leu  Glu  Arg  Ala  Arg  Arg  Gly  Glu  Gly  Pro
145                      150                      155                      160

Thr  Leu  Val  Glu  Ala  Phe  Thr
                    165
```

( 2 ) INFORMATION FOR SEQ ID NO:6:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Leu  Ala  Glu  Ser  Gly  Ile  Val  Gly  Thr  Ala  Ile  Gly  Leu  Ala  Leu  Arg
 1              5                        10                       15

Gly  Tyr  Arg  Pro  Val  Val  Glu  Ile  Gln  Phe  Asp  Gly  Phe  Val  Phe  Pro
               20                        25                       30
```

-continued

```
Ala  Tyr  Asp  Gln  Ile  Val  Thr  Gln  Leu  Ala  Lys  Met  His  Ala  Arg  Ala
          35                      40                     45

Ser  Gly  Lys  Ile  Lys  Leu  Pro  Val  Val  Val  Arg  Ile  Pro  Tyr  Gly  Gly
     50                      55                      60

Gly  Ile  Gly
65
```

(2) INFORMATION FOR SEQ ID NO:7:

(i) SEQUENCE CHARACTERISTICS:
       (A) LENGTH: 63 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:7:

```
Pro  Val  Phe  Leu  Gly  Gly  Gly  Pro  Pro  Glu  Ile  Ala  Ala  Arg  Ile  Thr
1                    5                      10                     15

Glu  Arg  Cys  Phe  Tyr  His  Leu  Glu  Ala  Pro  Val  Leu  Arg  Val  Gly  Gly
               20                      25                     30

Tyr  His  Ala  Pro  Tyr  Pro  Pro  Ala  Arg  Leu  Glu  Glu  Glu  Tyr  Leu  Pro
          35                      40                     45

Gly  Leu  Asp  Arg  Val  Leu  Asp  Ala  Val  Asp  Arg  Ser  Leu  Ala  Tyr
     50                      55                      60
```

(2) INFORMATION FOR SEQ ID NO:8:

(i) SEQUENCE CHARACTERISTICS:
       (A) LENGTH: 150 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:8:

```
Asn  Gln  Glu  Ile  Val  Leu  Lys  His  Tyr  Val  Asn  Leu  Gly  Ile  Ala  Ala
1                    5                      10                     15

Ala  Thr  Pro  Arg  Gly  Leu  Ile  Val  Pro  Asn  Ile  Lys  Asp  Ala  His  Ala
               20                      25                     30

Lys  Thr  Val  Pro  Gln  Leu  Ala  Glu  Ser  Leu  Gly  Glu  Leu  Val  Ser  Thr
          35                      40                     45

Ala  Arg  Glu  Gly  Lys  Thr  Ser  Pro  Thr  Ala  Met  Gln  Gly  Gly  Thr  Val
     50                      55                      60

Thr  Ile  Thr  Asn  Val  Gly  Val  Leu  Arg  Arg  Arg  His  Gly  His  Ala  Asp
65                   70                      75                          80

Pro  Ile  Leu  Asn  Pro  Gly  Glu  Ser  Ala  Ile  Leu  Gly  Phe  Gly  Ala  Ile
               85                      90                     95

Lys  Leu  Gln  Pro  Trp  Val  His  Lys  Gly  Lys  Val  Lys  Pro  Arg  Gln  Val
               100                     105                    110

Thr  Thr  Leu  Ala  Leu  Ser  Phe  Asp  His  Arg  Leu  Val  Asp  Gly  Glu  Leu
          115                     120                    125

Gly  Ser  Lys  Val  Leu  Ala  Asp  Val  Ala  Ala  Ile  Leu  Glu  Gln  Pro  Lys
     130                     135                    140

Arg  Leu  Ile  Thr  Trp  Ala
145                  150
```

(2) INFORMATION FOR SEQ ID NO:9:

( i ) SEQUENCE CHARACTERISTICS:
  ( A ) LENGTH: 41 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:9:

AAGAATTCGA GCTCGGCGAC GGCGCCACCT CCGAGGGCGA C                41

( 2 ) INFORMATION FOR SEQ ID NO:10:

( i ) SEQUENCE CHARACTERISTICS:
  ( A ) LENGTH: 38 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:10:

AAGGATCCTC TAGAGGTSSW GTGGKGGCCG ATSCGGWA                    38

( 2 ) INFORMATION FOR SEQ ID NO:11:

( i ) SEQUENCE CHARACTERISTICS:
  ( A ) LENGTH: 37 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:11:

AAGGATCCTG CAGCCCAGTC ACGACGTTGT AAAACGA                     37

( 2 ) INFORMATION FOR SEQ ID NO:12:

( i ) SEQUENCE CHARACTERISTICS:
  ( A ) LENGTH: 37 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:12:

AAGGATCCTG CAGACAGCTA TGACCATGAT TACGCCA                     37

( 2 ) INFORMATION FOR SEQ ID NO:13:

( i ) SEQUENCE CHARACTERISTICS:
  ( A ) LENGTH: 17 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:13:

GTAGGGAGCC TGATATG                                           17

( 2 ) INFORMATION FOR SEQ ID NO:14:

( i ) SEQUENCE CHARACTERISTICS:
  ( A ) LENGTH: 17 base pairs
  ( B ) TYPE: nucleic acid
  ( C ) STRANDEDNESS: double -continued ( D ) TOPOLOGY: linear ( i i ) MOLECULE TYPE: cDNA ( x i ) SEQUENCE DESCRIPTION: SEQ ID NO:14:

GCTATCCGCG CATCCAT 17

We claim:

1. A method of producing a natural avermectin comprising fermenting *S. avermitilis* in which the copy number of a genomic fragment comprising one or more of the bkdF, bkdG and bkdH genes has been increased.

2. A method according to claim 1, comprising fermenting *S. avermitilis* in which the copy number of a genomic fragment comprising the bkdF, bkdG and bkdH genes have been increased.

* * * * *